US012150631B2

(12) United States Patent
Cohen et al.

(10) Patent No.: US 12,150,631 B2
(45) Date of Patent: Nov. 26, 2024

(54) SURGICAL ARTICULATED ARM

(71) Applicant: MEMIC INNOVATIVE SURGERY LTD, Or-Yehuda (IL)

(72) Inventors: Dvir Cohen, Ramot-Menashe (IL); Yaron Levinson, Tel-Aviv (IL); Yiftah Neta, Gilon (IL)

(73) Assignee: Momentis Surgical Ltd., Or-Yehuda (IL)

( * ) Notice: Subject to any disclaimer, the term of this patent is extended or adjusted under 35 U.S.C. 154(b) by 1025 days.

(21) Appl. No.: 16/972,600

(22) PCT Filed: Jun. 13, 2019

(86) PCT No.: PCT/IL2019/050671
§ 371 (c)(1),
(2) Date: Dec. 6, 2020

(87) PCT Pub. No.: WO2019/244147
PCT Pub. Date: Dec. 26, 2019

(65) Prior Publication Data
US 2021/0236234 A1  Aug. 5, 2021

Related U.S. Application Data

(60) Provisional application No. 62/686,023, filed on Jun. 17, 2018.

(51) Int. Cl.
*A61B 17/00* (2006.01)
*A61B 17/29* (2006.01)
*A61B 34/00* (2016.01)

(52) U.S. Cl.
CPC ........ *A61B 17/00234* (2013.01); *A61B 34/71* (2016.02); *A61B 2017/00309* (2013.01);
(Continued)

(58) Field of Classification Search
CPC ... A61B 17/00234; A61B 2017/00238–00362; A61B 34/30–77
See application file for complete search history.

(56) References Cited

U.S. PATENT DOCUMENTS 6,723,106 B1   4/2004  Charles
7,766,821 B2   8/2010  Brunnen
(Continued)

FOREIGN PATENT DOCUMENTS

WO    2016/035084 A2   3/2016
WO    2019/244147 A1   12/2019

OTHER PUBLICATIONS

International Search Report for PCT/IB2020/058292 document completed Jan. 11, 2021.
(Continued)

*Primary Examiner* — Thaddeus B Cox
(74) *Attorney, Agent, or Firm* — S. J. INTELLECTUAL PROPERTY; Avi Jencmen

(57) ABSTRACT

An articulated arm including: a tubular structure comprising a plurality of coupled longitudinal sections including: at least one rigid portion; and at least one flexible portion comprising a plurality of connected annular portions; wherein the tubular structure includes: a trench formed along a long axis of the tubular structure and extending along the plurality of coupled longitudinal sections; and a cover attached to the tubular structure and covering at least a portion of the trench.

10 Claims, 15 Drawing Sheets

(52) U.S. Cl.
CPC ............... *A61B 2017/00314* (2013.01); *A61B 2017/00327* (2013.01); *A61B 2017/00526* (2013.01); *A61B 17/29* (2013.01)

(56) References Cited

U.S. PATENT DOCUMENTS

| | | | |
|---|---|---|---|
| 8,721,630 B2 | 5/2014 | Ortiz | |
| 9,039,057 B2 | 5/2015 | Schvalb | |
| 9,788,911 B2 | 10/2017 | Cohen | |
| 9,820,822 B2 | 11/2017 | Cohen | |
| 10,022,196 B2 | 7/2018 | Griffiths | |
| 10,022,197 B2 | 7/2018 | Cohen | |
| 10,052,165 B2 | 8/2018 | Cohen | |
| 10,070,930 B2 | 9/2018 | Cohen | |
| 10,299,866 B2 | 5/2019 | Cohen | |
| 10,470,831 B2 | 11/2019 | Cohen | |
| 10,500,003 B2 | 12/2019 | Cohen | |
| 10,617,481 B2 | 4/2020 | Cohen | |
| 10,736,658 B2 | 8/2020 | Cohen | |
| 10,849,654 B2 | 12/2020 | Cohen | |
| 10,869,692 B2 | 12/2020 | Cohen | |
| 10,973,592 B2 | 4/2021 | Cohen | |
| 2004/0138700 A1 | 7/2004 | Cooper | |
| 2007/0055103 A1 | 3/2007 | Hoefig | |
| 2007/0151391 A1* | 7/2007 | Larkin | A61B 34/76 74/490.06 |
| 2007/0221700 A1 | 9/2007 | Ortiz | |
| 2008/0004606 A1 | 1/2008 | Swain | |
| 2008/0021440 A1 | 1/2008 | Solomon | |
| 2008/0065098 A1 | 3/2008 | Larkin | |
| 2009/0095112 A1* | 4/2009 | Buckingham | B25J 9/104 901/28 |
| 2009/0247993 A1 | 10/2009 | Kirschenman | |
| 2010/0280543 A1* | 11/2010 | Kim | A61B 34/72 606/1 |
| 2011/0270081 A1 | 11/2011 | Burg | |
| 2011/0313245 A1 | 12/2011 | Scholly | |
| 2012/0186383 A1 | 7/2012 | Schvalb | |
| 2012/0265220 A1 | 10/2012 | Menn | |
| 2014/0088361 A1 | 3/2014 | Hrayr | |
| 2014/0236083 A1 | 8/2014 | Sims | |
| 2015/0066002 A1 | 3/2015 | Cooper | |
| 2015/0313452 A1 | 11/2015 | Hasser | |
| 2015/0327940 A1 | 11/2015 | Inoue | |
| 2016/0074028 A1 | 3/2016 | Castro | |
| 2016/0080701 A1 | 3/2016 | Henn | |
| 2016/0213435 A1 | 7/2016 | Hourtash | |
| 2016/0242860 A1 | 8/2016 | Diolaiti | |
| 2017/0071687 A1 | 3/2017 | Cohen | |
| 2017/0071688 A1 | 3/2017 | Cohen | |
| 2017/0079731 A1 | 3/2017 | Griffiths | |
| 2017/0086932 A1 | 3/2017 | Auld | |
| 2017/0112581 A1 | 4/2017 | Cohen | |
| 2017/0112583 A1 | 4/2017 | Cohen | |
| 2017/0119483 A1 | 5/2017 | Cohen | |
| 2017/0135776 A1 | 5/2017 | Cohen | |
| 2017/0231701 A1 | 8/2017 | Cohen | |
| 2017/0239005 A1 | 8/2017 | Cohen | |
| 2017/0258538 A1 | 9/2017 | Cohen | |
| 2017/0258539 A1 | 9/2017 | Cohen | |
| 2017/0334067 A1 | 11/2017 | Swarup | |
| 2018/0256235 A1 | 9/2018 | Cohen | |
| 2018/0256241 A1 | 9/2018 | Cohen | |
| 2018/0256246 A1 | 9/2018 | Cohen | |
| 2018/0256265 A1 | 9/2018 | Cohen | |
| 2018/0256266 A1 | 9/2018 | Cohen | |
| 2018/0256267 A1 | 9/2018 | Cohen | |
| 2018/0256268 A1 | 9/2018 | Cohen | |
| 2019/0000574 A1 | 1/2019 | Cohen | |
| 2019/0059868 A1 | 2/2019 | Cohen | |
| 2019/0059939 A1 | 2/2019 | Cohen | |
| 2019/0059940 A1 | 2/2019 | Cohen | |
| 2019/0059941 A1 | 2/2019 | Cohen | |
| 2019/0083193 A1 | 3/2019 | Cohen | |
| 2019/0167363 A1 | 6/2019 | Cohen | |
| 2019/0167364 A1 | 6/2019 | Cohen | |
| 2019/0231445 A1 | 8/2019 | Cohen | |
| 2020/0289225 A1 | 9/2020 | Cohen | |
| 2021/0059716 A1 | 3/2021 | Cohen | |
| 2021/0196407 A1 | 7/2021 | Cohen | |
| 2021/0236234 A1 | 8/2021 | Cohen | |
| 2021/0338345 A1 | 11/2021 | Cohen | |
| 2022/0054205 A1 | 2/2022 | Cohen | |
| 2022/0331003 A1 | 10/2022 | Cohen | |
| 2023/0000571 A1 | 1/2023 | Cohen | |
| 2023/0000579 A1 | 1/2023 | Cohen | |

OTHER PUBLICATIONS

International Search Report for PCT/IL2019/050671 document completed Sep. 25, 2019.
Written Opinion for PCT/IB2020/058292 document completed Jan. 11, 2021.
Written Opinion for PCT/IL2019/050671 document completed Sep. 25, 2019.

\* cited by examiner

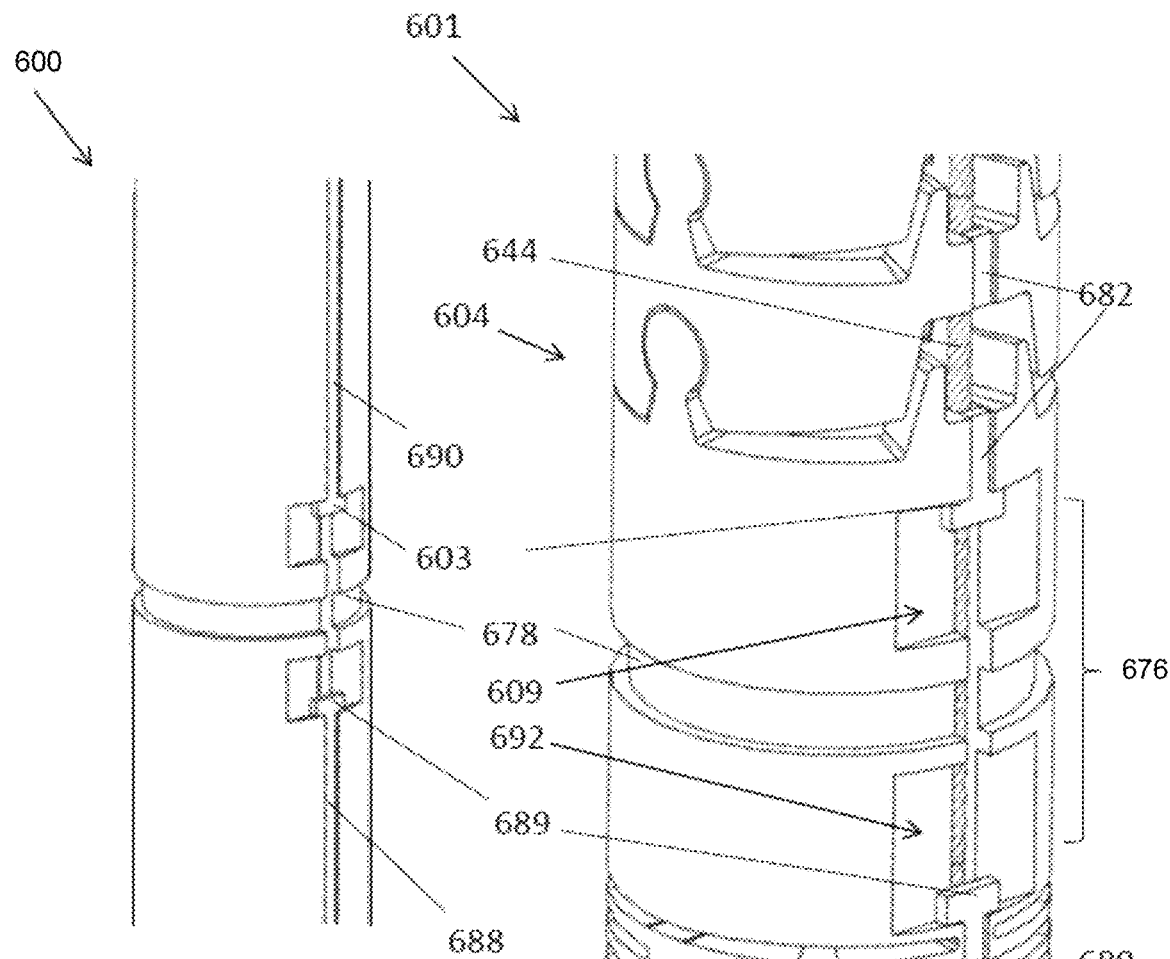
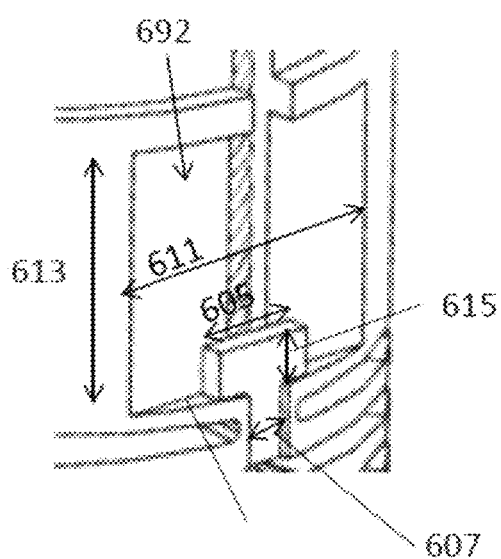
FIG. 6A
FIG. 6B
FIG. 6C

SURGICAL ARTICULATED ARM

RELATED APPLICATIONS

This application claims the benefit of priority under 35 USC § 119(e) of U.S. Provisional Patent Application No. 62/686,023 filed 17 Jun. 2018, the contents of which are incorporated herein by reference in their entirety.

This application is related to PCT Patent Application Nos. PCT/IL2015/050891, PCT/IL2015/050892, PCT/IL2015/050893 and PCT/IL2016/050976, U.S. Patent Application Publication No. 2017-0258539-A1 and U.S. Provisional Application Nos. 62/468,507, 62/583,540 and 62/583,543.

The contents of the above applications are all incorporated by reference as if fully set forth herein in their entirety.

FIELD AND BACKGROUND OF THE INVENTION

The present invention, in some embodiments thereof, relates to an articulated mechanical arm, robust and accurate mechanical control of the arm and, more particularly, but not exclusively, to an articulated mechanical arm which maintains its mechanical integrity under repetitive movement.

U.S. Pat. No. 7,862,580 discloses "The present invention is directed to a tool having a wrist mechanism that provides pitch and yaw rotation in such a way that the tool has no singularity in roll, pitch, and yaw. In one embodiment, a minimally invasive surgical instrument comprises an elongate shaft having a working end, a proximal end, and a shaft axis between the working end and the proximal end; and an end effector. A wrist member has a flexible tube including an axis extending through an interior surrounded by a wall. The wall of the flexible tube includes a plurality of lumens oriented generally parallel to the axis of the flexible tube. The wrist member has a proximal portion connected to the working end of the elongate shaft and a distal portion connected to the end effector. A plurality of actuation cables have distal portions connected to the end effector and extend from the distal portion through the lumens of the wall of the wrist member toward the elongate shaft to proximal portions which are actuatable to bend the wrist member in pitch rotation and yaw rotation."

SUMMARY OF THE INVENTION

Following are examples of some embodiments of the invention. Features of one example may be combined with features of one or more other examples, unless expressly prohibited and form additional examples of some embodiments of the invention.

Example 1. An articulated arm comprising:
a tubular structure comprising a plurality of coupled longitudinal sections comprising:
at least one rigid portion; and
at least one flexible portion comprising a plurality of connected annular portions;
wherein said tubular structure comprises:
a trench formed along a long axis of said tubular structure and extending along said plurality of coupled longitudinal sections; and
a cover attached to said tubular structure and covering at least a portion of said trench.

Example 2. The articulated arm according to Example 1, wherein said trench does not radially penetrate a wall of said tubular structure to an inner surface of the tubular structure.

Example 3. The articulated arm according to any one of Examples 1-2, wherein said cover completes said tubular structure to a tubular shape.

Example 4. The articulated arm according to any one of Examples 1-3, wherein an outer contour of said cover is contained by an outer contour of said tubular structure before cutting of said trench.

Example 5. The articulated arm according to any one of Examples 1-4, comprising at least one flange disposed at least a portion of at least one of edge of said trench, where said cover is attached to said at least one flange.

Example 6. The articulated arm according to Example 5, wherein said at least one flange is cut in said tube at an edge of said trench, to a smaller depth than said trench.

Example 7. The articulated arm according to any one of Example 1-4, wherein said cover is attached to the walls of said trench.

Example 8. The articulated arm according to any one of Examples 1-7, comprising an elongated element for control of said articulated arm, where said elongated element is:
disposed within said trench;
at least partially enclosed within said trench by said cover; and
coupled to a portion of said tubular structure distal of said at least one flexible portion.

Example 9. The articulated arm according to Example 8, wherein flexion of said flexible portion is controlled by changing tension on said elongated element.

Example 10. The articulated arm according to any one of Examples 1-8, comprising:
a second trench cut along a long axis of said tubular structure; and
a second cover attached to and covering said second trench.

Example 11. The articulated arm according to Example 10, wherein said second trench is circumferentially opposite said first trench.

Example 12. The articulated arm according to any one of Examples 10-11, comprising a second elongated element for control of said articulated arm, where said elongated element is:
disposed within said second trench;
at least partially enclosed within said second trench by said second cover; and
coupled to a portion of said tubular structure distal of said at least one flexible portion.

Example 13. The articulated arm according to Example 12, wherein flexion of said flexible portion is controlled by changing tension on said elongated element and said second elongated element.

Example 14. The articulated arm according to any one of Examples 1-13, wherein said cover includes at least one wide portion.

Example 15. The articulated arm according to Example 14, wherein said at least one wide portion is axially aligned with said at least one rigid portion.

Example 16. The articulated arm according to any one of Examples 14-15, wherein a dimension of said trench at a location of said at least one wide portion is sized and shaped to receive said wide portion.

Example 17. The articulated arm according to any one of Examples 1-13, wherein said cover includes a first and a second wide portion disposed at a proximal and a distal end of said cover respectively.

Example 18. The articulated arm according to Example 17 wherein said first and said second wide portion are each axially disposed at a rigid portion of said tubular structure.

Example 19. The articulated arm according to any one of Examples 1-18 comprising a second tubular structure disposed within a central hollow passageway of said first tubular structure.

Example 20. An articulated arm comprising:
a first tubular structure comprising:
a first tubular structure flexible portion;
at least one first tubular structure rigid portion;
a central hollow passageway;
at least one first tubular structure hollow passageway within and occupying a radial portion of a wall of said first tubular structure and extending along a long axis of said first tubular structure;
a second tubular structure including at least a portion disposed within said central hollow passageway comprising a bendable portion axially aligned with said first tubular structure flexible portion.

Example 21. The articulated arm according to Example 20, wherein said second tubular structure comprises a second tubular structure flexible portion.

Example 22. The articulated arm according to any one of Examples 20-21, wherein said second tubular structure comprises at least one second tubular structure rigid portion.

Example 23. The articulated arm according to Example 20, wherein said second tubular structure comprises at least one hollow passageway within and occupying a radial portion of a wall of said second tubular structure and extending along a long axis of said first tubular structure.

Example 24. An articulated arm comprising:
an elongate tubular structure comprising:
a bendable portion comprising:
a plurality of connected annular portions;
a plurality of connectors, each annular portion connected to an adjacent annular portion by a connector;
a plurality of connector hollow passageways, each said connector comprising a connector hollow passageway;
a rigid portion coupled to said bendable portion and comprising a rigid portion hollow passageway; and
a control cable coupled to said elongate tubular structure distal of said bendable portion, disposed within and extending through said rigid portion hollow passageway and said plurality of connector hollow passageways.

Example 25. The articulated arm according to Example 24, wherein said connectors extend in a direction of a long axis of said tubular structure.

Example 26. The articulated arm according to any one of Examples 24-25, wherein said tubular structure comprises a flexible section distal of said bendable portion;
wherein said control cable is coupled to said tubular structure distal of a most proximal portion of said flexible section;
wherein changing tension on said control cable actuates bending of said flexible section.

Example 27. The articulated arm according to any one of Examples 24-26, comprising:
a second tubular structure comprising:
a second tubular structure central hollow passageway in which at least a portion of said tubular structure is disposed;
a second tubular structure flexible portion, where said tubular structure bendable portion is axially aligned with said second tubular structure flexible portion and where flexion of said second tubular structure flexible portion thereby bends said bendable portion.

Example 28. An articulated arm comprising:
an end effector;
a shaped support structure including a trench which extends longitudinally along and circumferentially around said support structure;
an electrical supply cable sitting within at least a portion of said trench, said electrical supply cable extending longitudinally along and circumferentially around said support structure.

Example 29. The articulated arm according to Example 28, comprising a tubular structure which extends longitudinally along said articulated arm wherein said shaped support structure and said electrical supply cable are disposed within a hollow passageway of said tubular structure.

Example 30. The articulated arm according to any one of Examples 28-29, comprising a control cable;
wherein said shaped support structure comprises a support structure hollow passageway extending longitudinally through at least a portion of said support structure and where at least a portion of said control cable is disposed within said support structure hollow passageway.

Example 31. The articulated arm according to Example 30, wherein said control cable is coupled to and configured to actuate said end effector.

Example 32. The articulated arm according to Example 31, wherein said control cable is a torque cable configured to transfer torque to said end effector to actuate said end effector.

Example 33. The articulated arm according to any one of Examples 28-32, wherein said trench is helical in shape around said shaped support structure, for at least a portion of a length of said support structure.

Example 34. A method of manufacture of an articulated arm comprising:
providing a tubular structure;
cutting a trench along a length of said tubular structure;
covering said trench with a cover; and
cutting at least a portion of said length of said tubular structure into segments to form a segmented articulation.

Example 35. The method according to Example 34, wherein said cutting at least a portion of said length of said tubular structure is by laser cutting.

Example 36. The method according to any one of Examples 34-35 wherein said covering is by laser welding said cover in position on said tubular structure to cover said trench.

Example 37. The method according to any one of Examples 34-36, wherein said cutting a trench comprises cutting one or more wider portion.

Example 38. The method according to Example 37, wherein said cover includes one or more wider portion sized and shaped to fit into said trench one or more wider portion.

Example 39. The method according to any one of Examples 34-38, comprising inserting a control cable into said trench.

Example 40. An articulated arm comprising a tubular structure comprising:
at least one bendable portion comprising a plurality of coupled portions separated by spaces, said coupled portions each including a hollow passageway extending in an axial direction;

a control cable extending in said axial direction where 30-70% of a length of said control cable extending along said bendable portion is disposed within said hollow passageways.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as collecting dental measurements, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 3A:
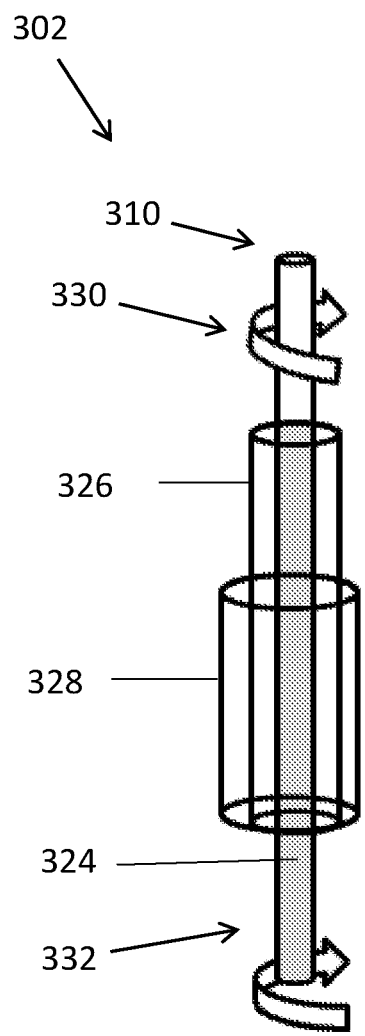
Figure 3B:
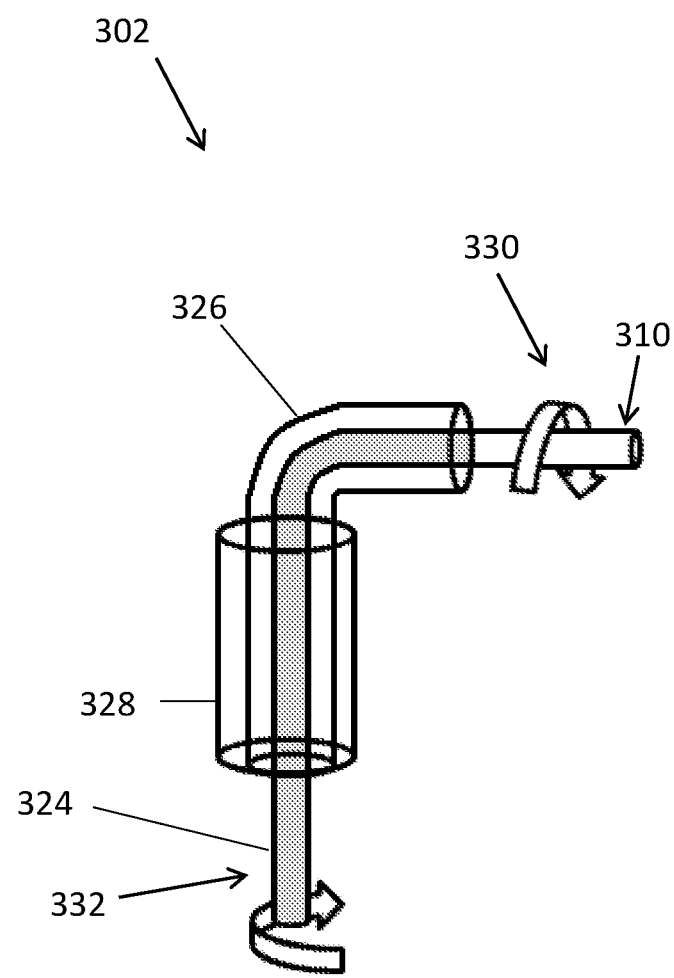
Figures 4A, 4B:
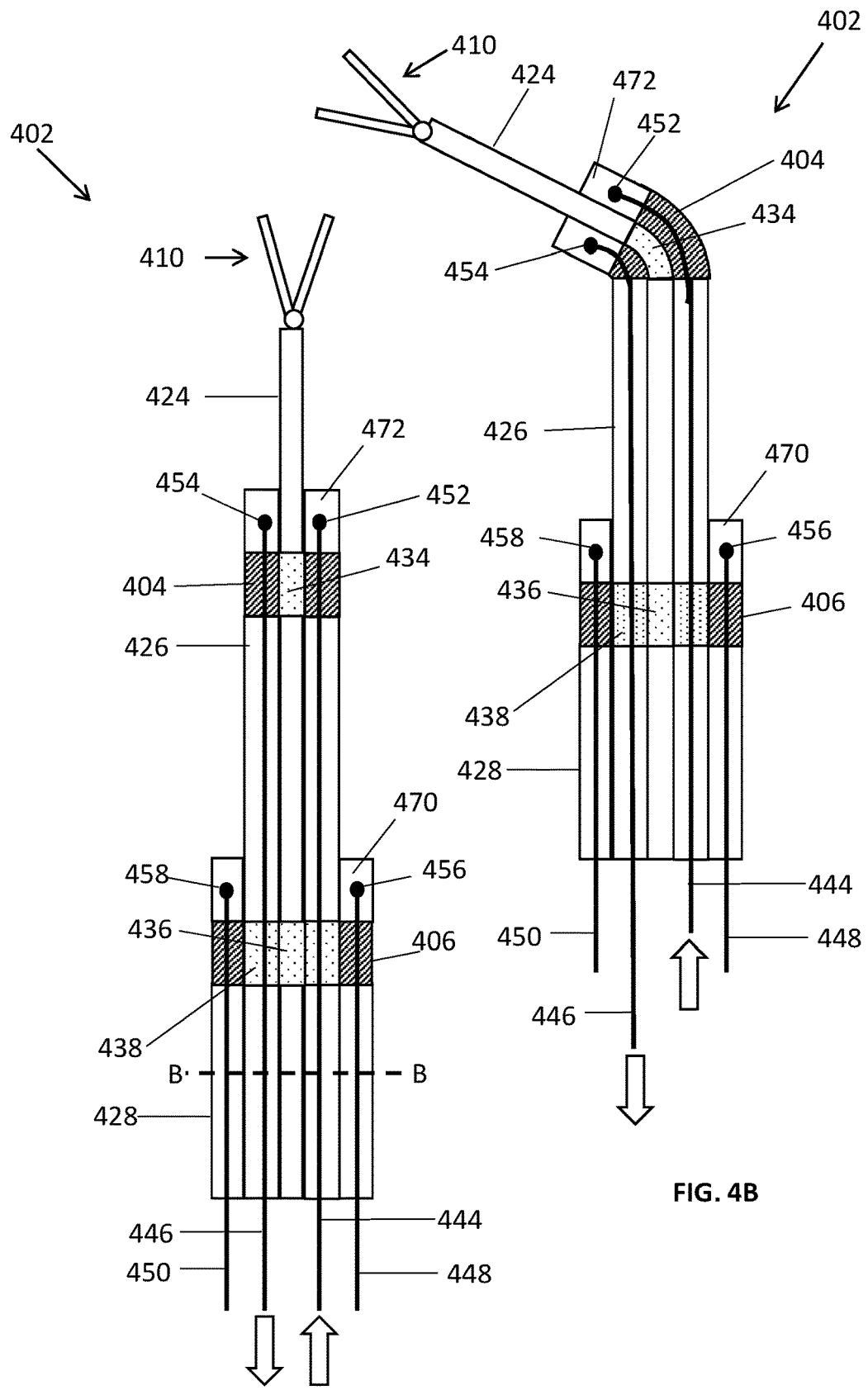
Figure 5A:
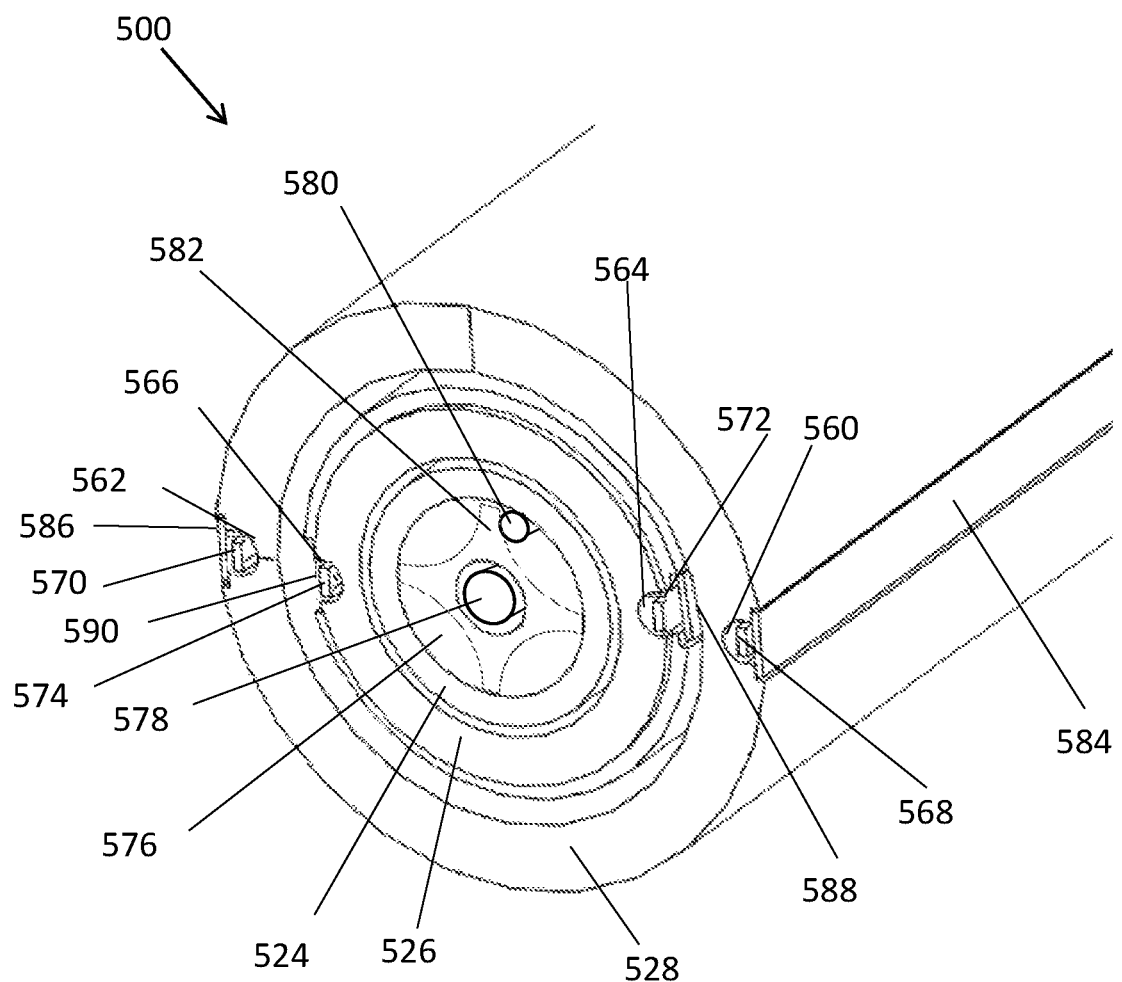
Figure 6D:
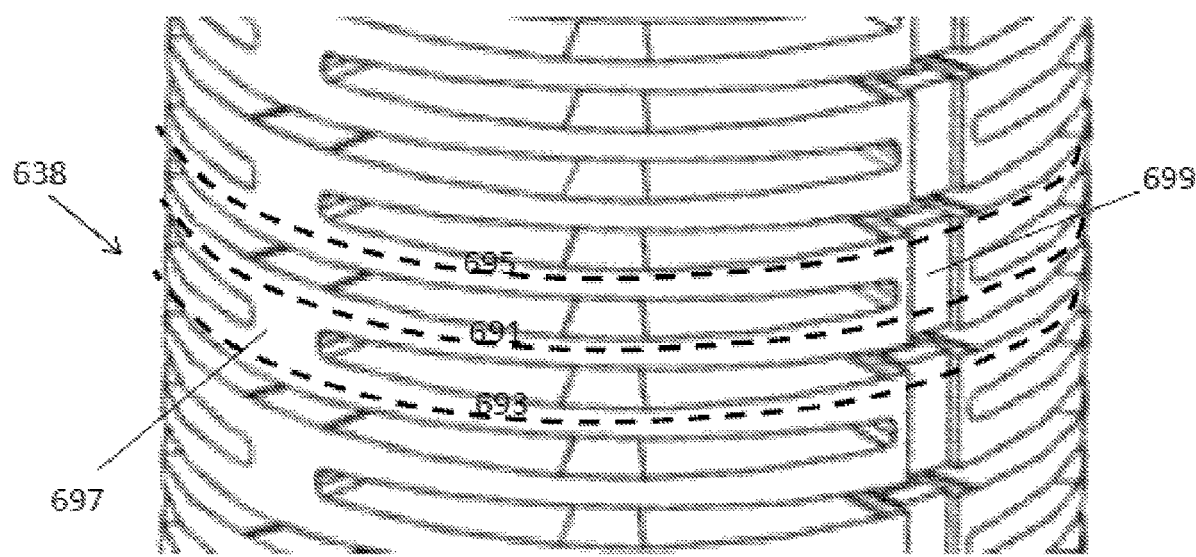
Figure 6E:
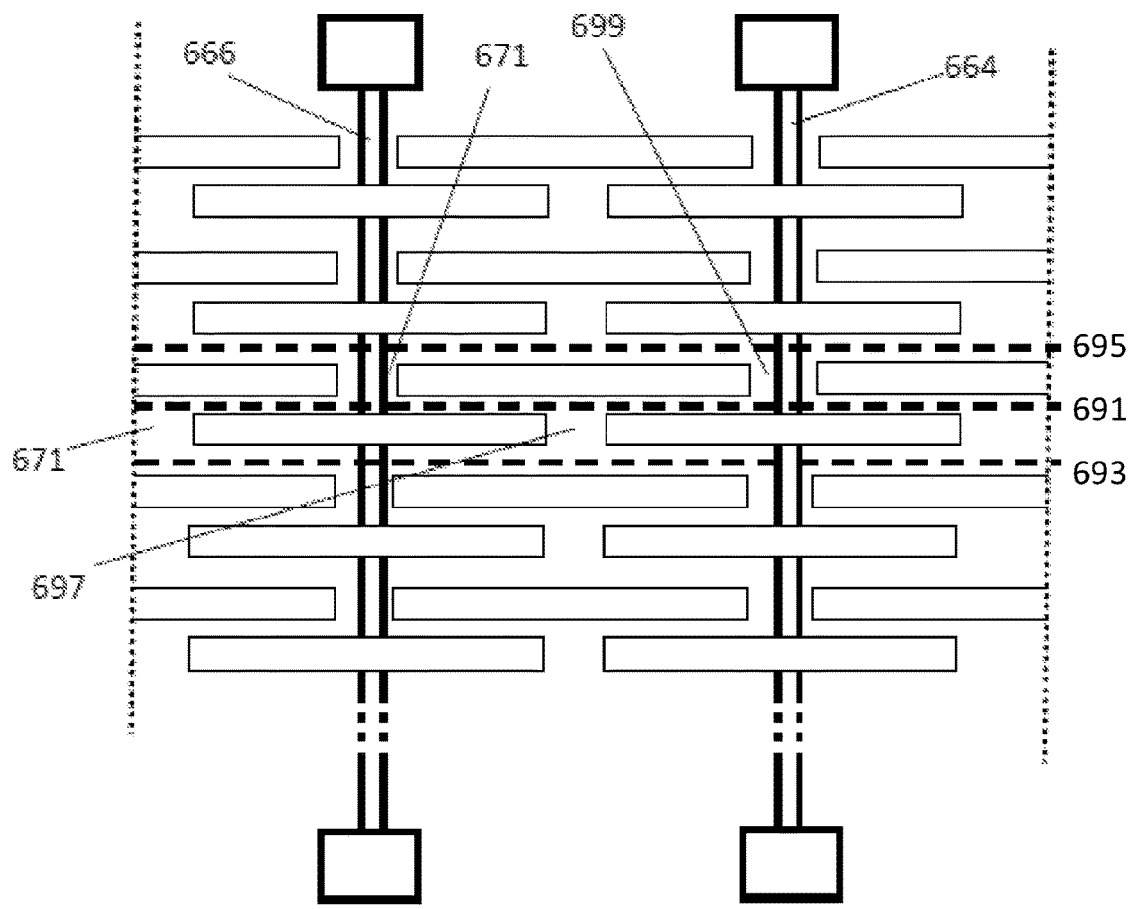
Figure 7A:
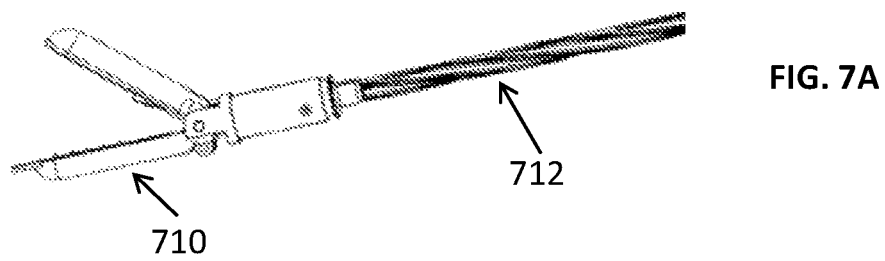
Figure 7B:
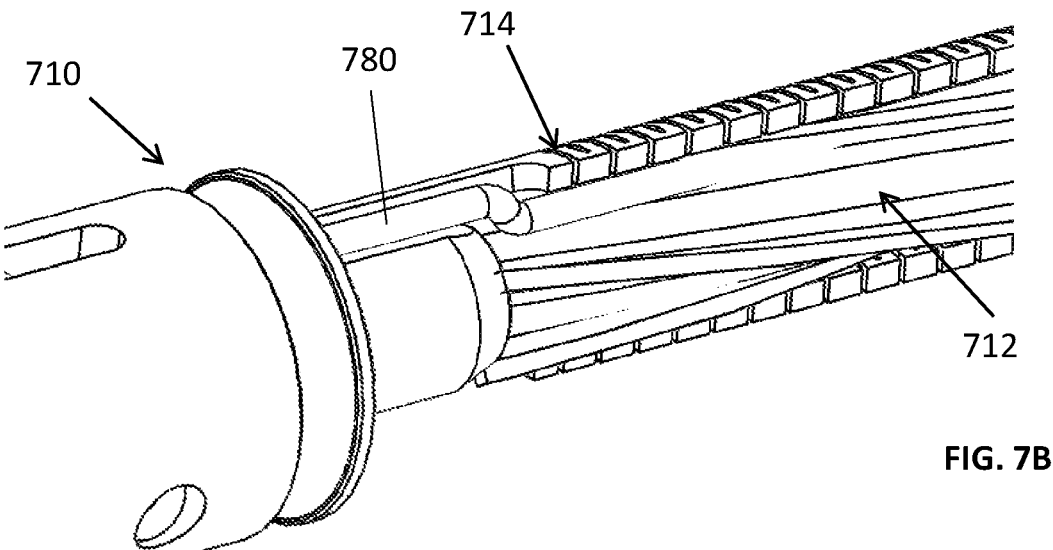
Figure 7C:
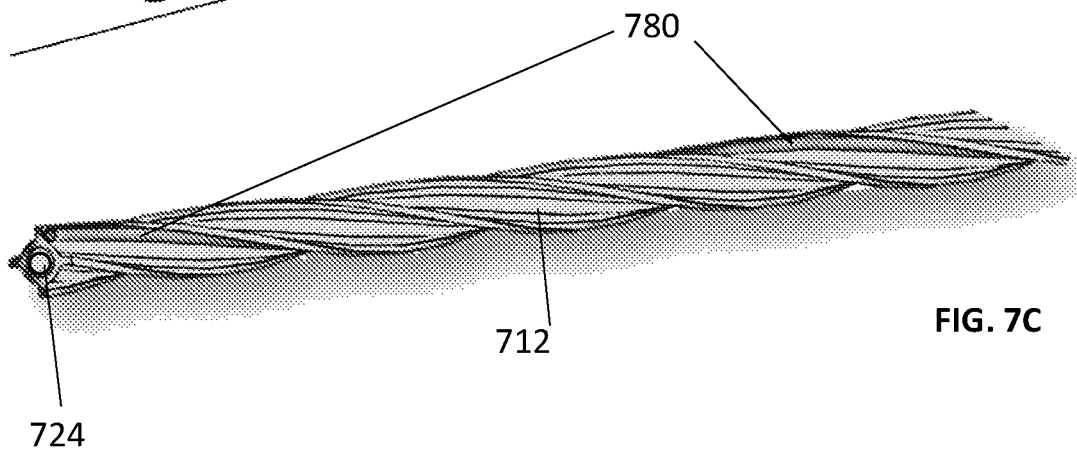
Figure 7D:
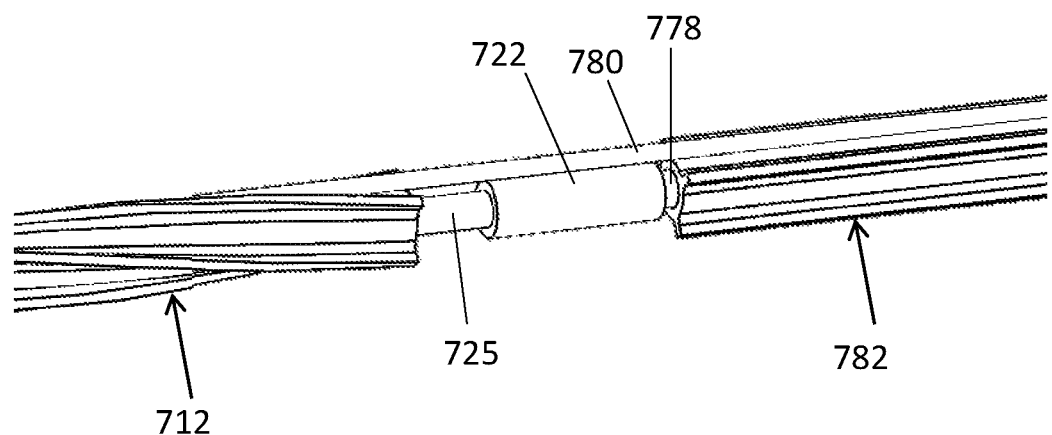
Figures 8A, 8B:
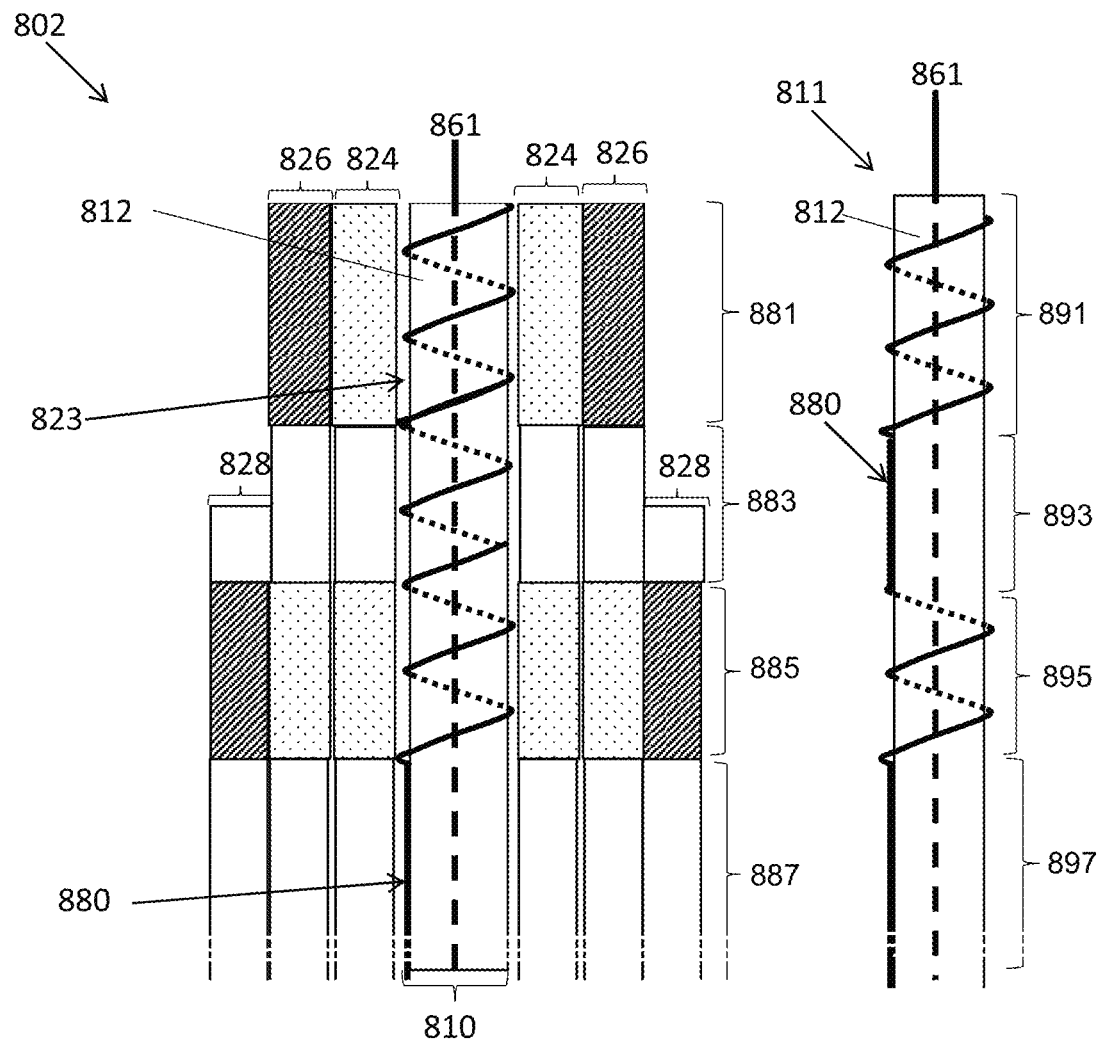
Figure 9A:
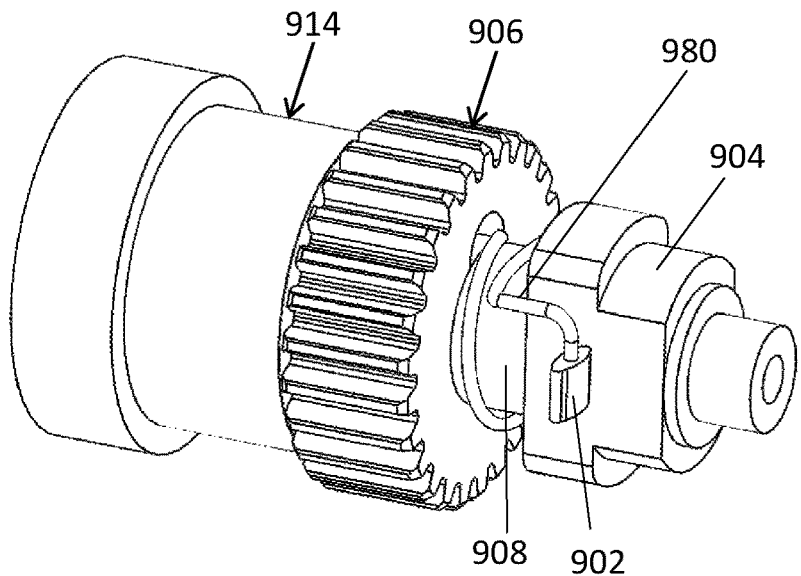
Figure 9B:
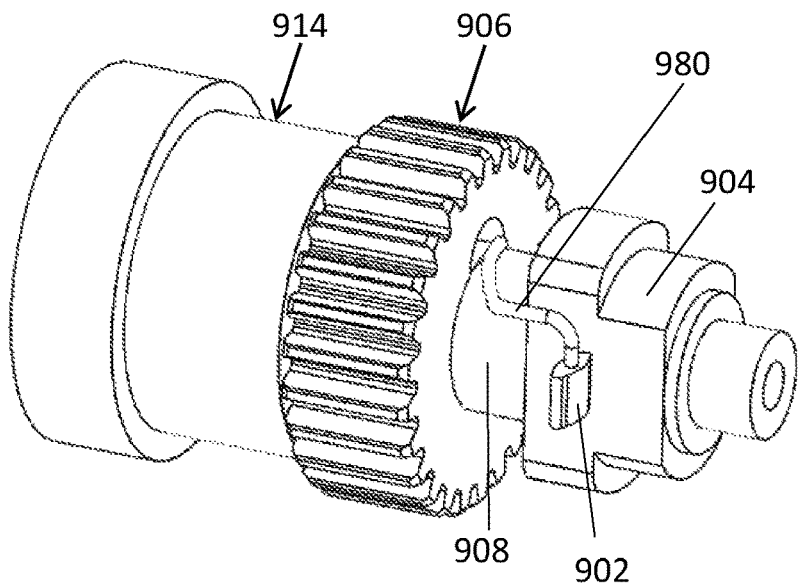
Figure 9C:
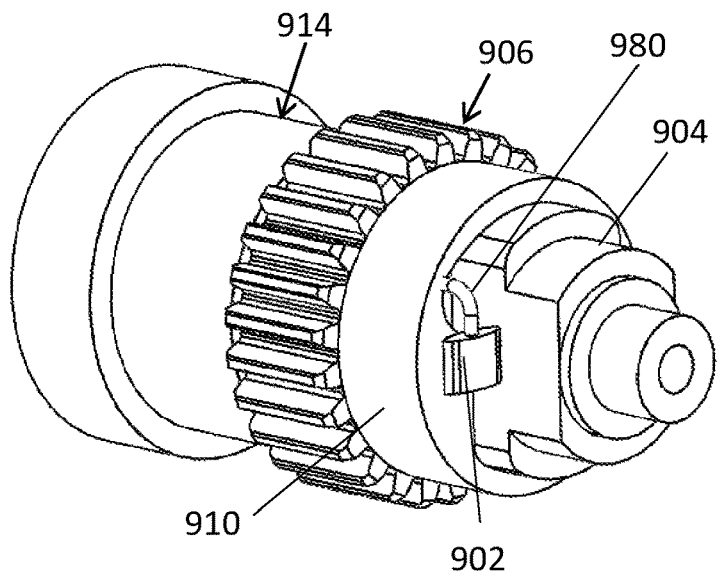
Figure 10A:
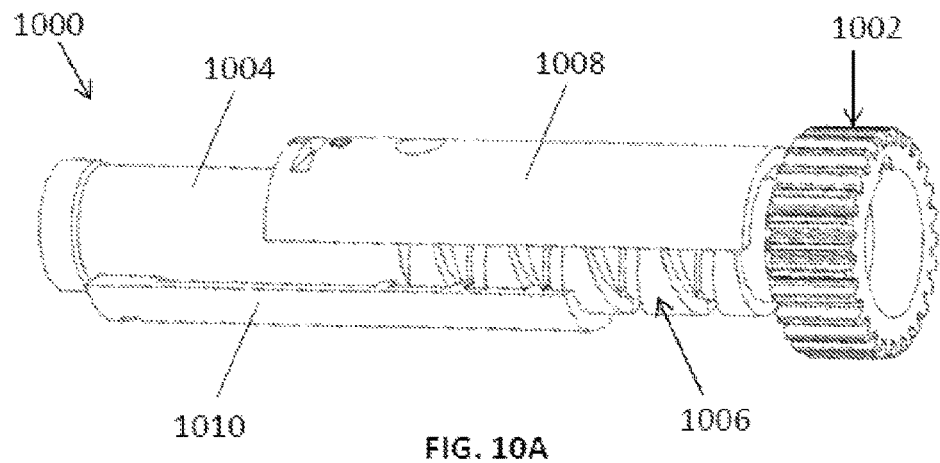
Figure 10B:
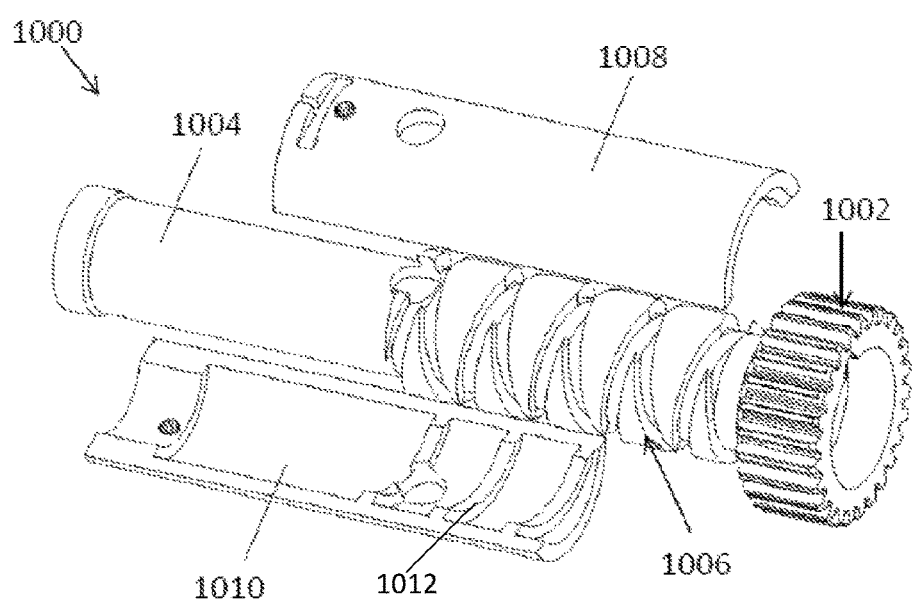
Figure 10C:
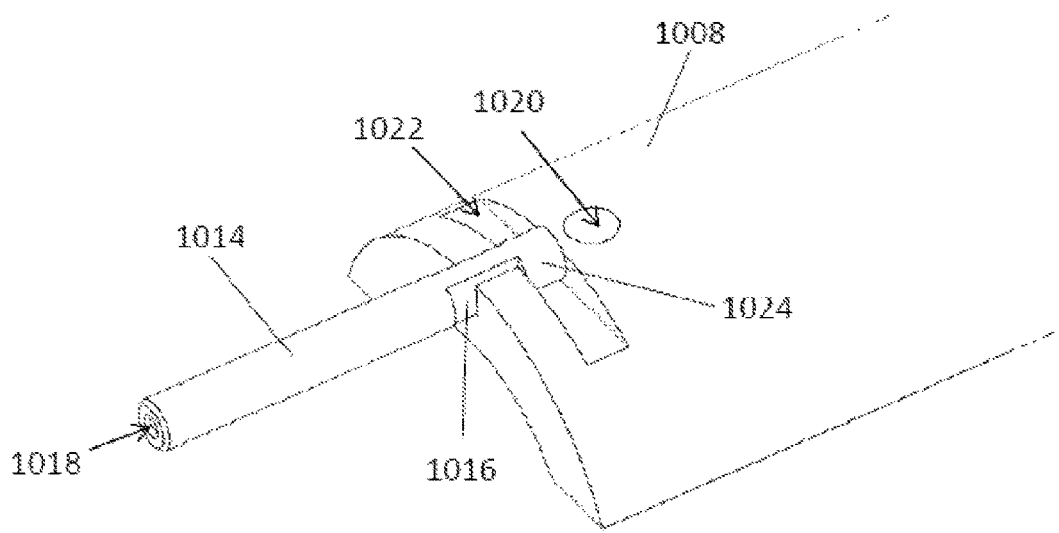
Figure 11:
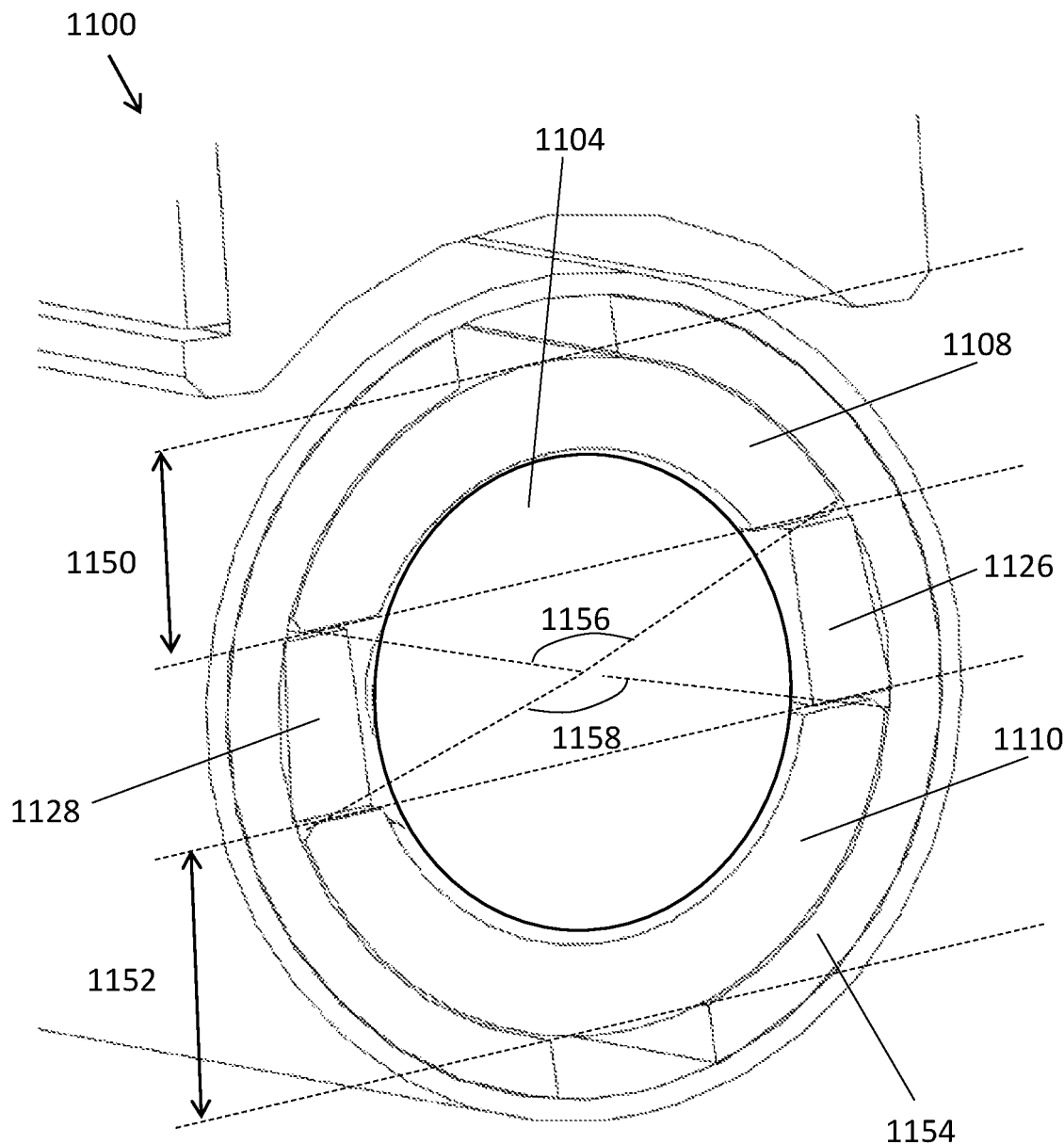
Figure 12:
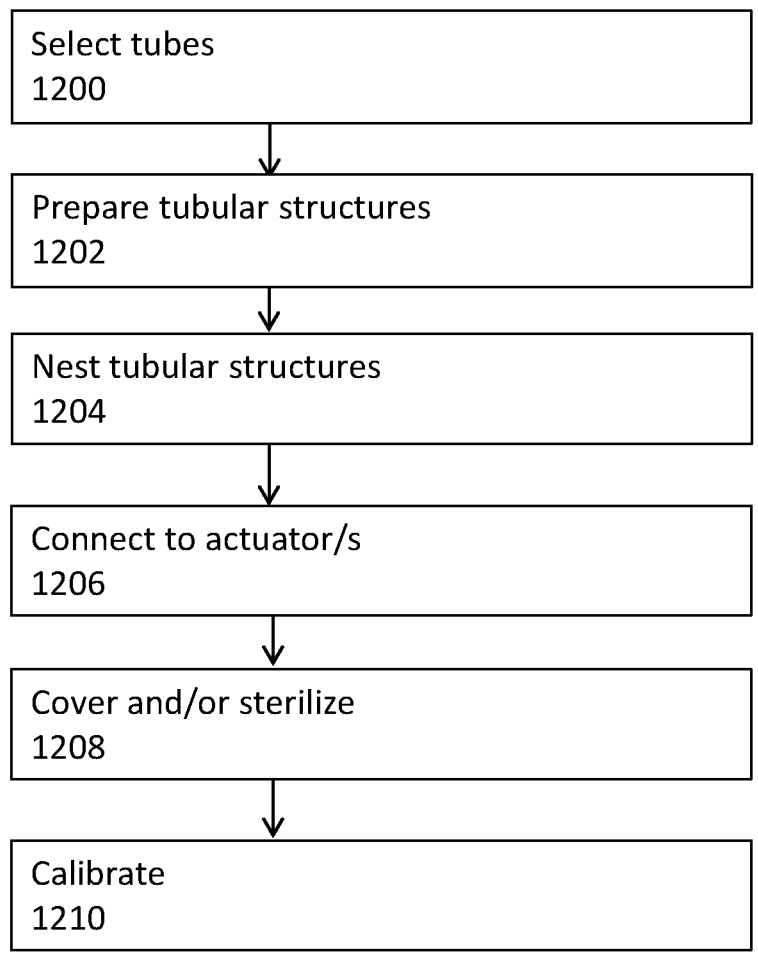
Figure 13:
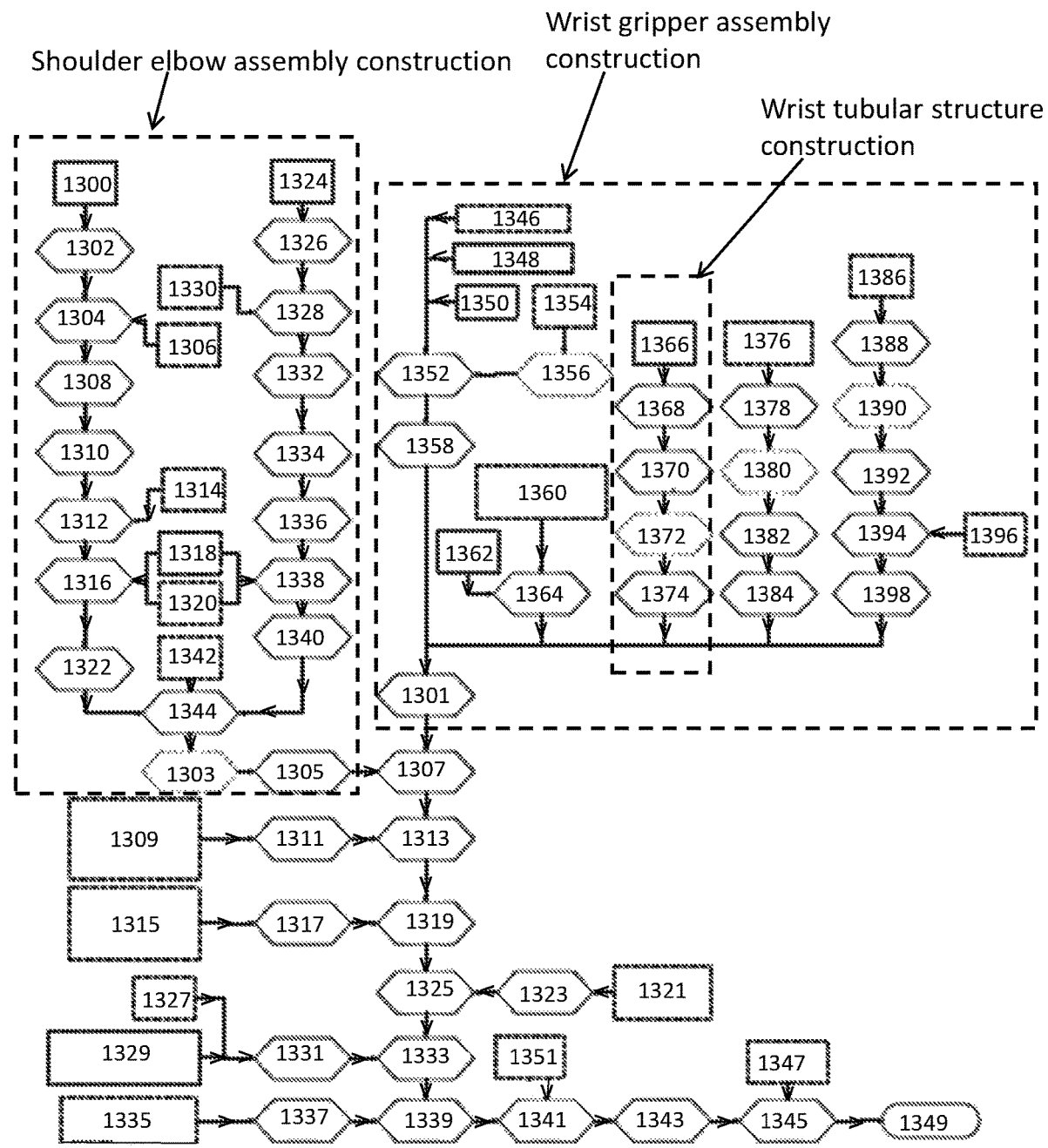
Figure 14A:
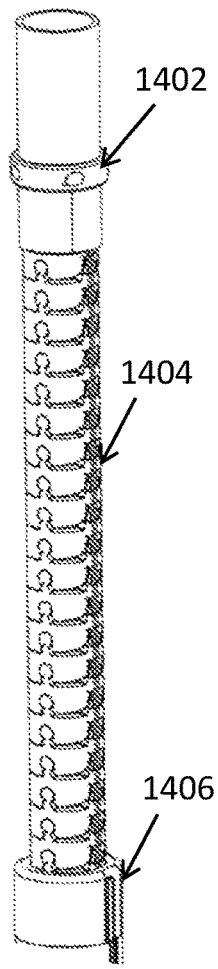
Figure 14B:
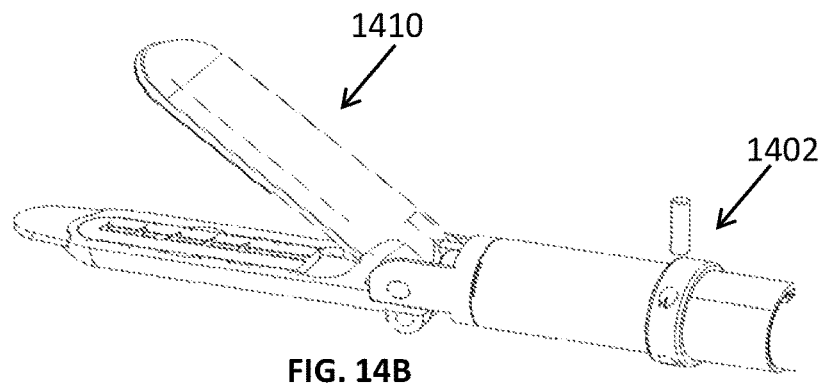
Figure 14C:
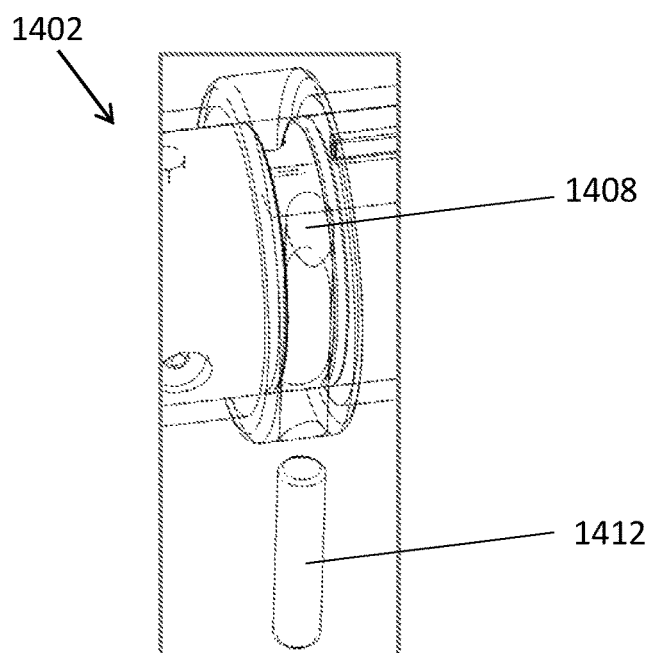
Figure 14D:
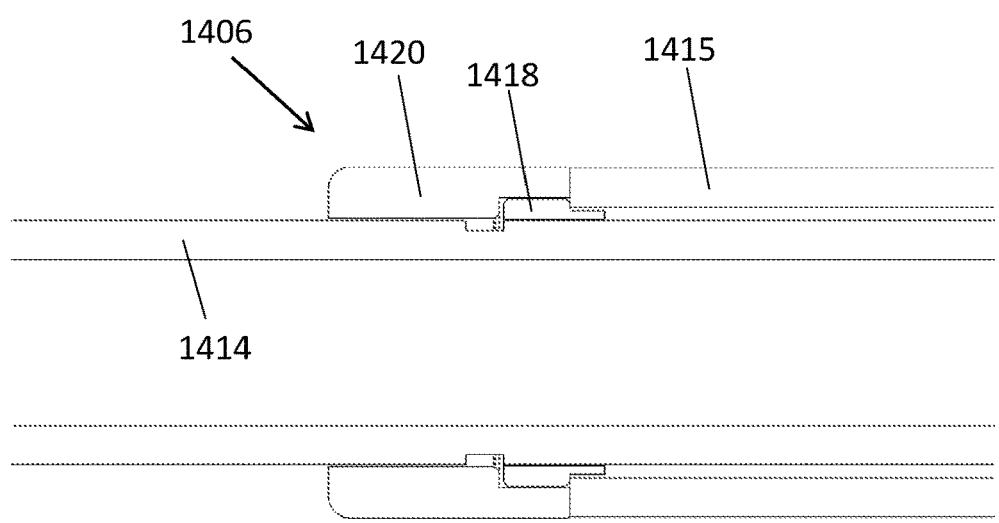

FIGS. 3A-B are simplified schematics of a mechanical arm, according to some embodiments of the invention;

FIGS. 4A-B are simplified schematic cross sections of a mechanical arm, according to some embodiments of the invention;

FIG. 5A is a simplified schematic section view of a mechanical arm, according to some embodiments of the invention;

FIGS. 5B-F are simplified schematic cross sections of tubular structure trenches, according to some embodiments of the invention;

FIG. 6A is a simplified schematic of a tubular structure, prior to laser cutting, according to some embodiments of the invention;

FIG. 6B is a simplified schematic of a tubular structure, after laser cutting, according to some embodiments of the invention;

FIG. 6C is an enlarged portion of FIG. 6B, according to some embodiments of the invention;

FIG. 6D is a simplified schematic of a portion of a torque transfer portion, according to some embodiments of the invention;

FIG. 6E is a simplified schematic plan view of a torque transfer portion 638, according to some embodiments of the invention;

FIG. 7A is a simplified schematic side view of an end effector and a portion of an end effector support structure, according to some embodiments of the invention;

FIG. 7B is a simplified schematic view of a portion of an end effector, a support structure and a sectional view of a tubular structure, according to some embodiments of the invention;

FIG. 7C is a simplified schematic view of a support structure coupled to a cable, according to some embodiments of the invention;

FIG. 7D is a simplified schematic view of a torque cable element including a torque cable and rigid shaft connected by a connector and support structures, according to some embodiments of the invention;

FIG. 8A is a simplified schematic of cross section of a portion of a mechanical arm, and a side view of an end effector assembly, according to some embodiments of the invention;

FIG. 8B is a simplified schematic side view of an end effector assembly, according to some embodiments of the invention;

FIGS. 9A-C are simplified views of embodiments of electrical connection of an electrical supply cable, according to some embodiments of the invention;

FIG. 10A is a simplified schematic view of a surgical mechanical arm actuator 1000, according to some embodiments of the invention;

FIG. 10B is a simplified exploded view of a surgical mechanical arm actuator 1000, according to some embodiments of the invention;

FIG. 10C is a simplified schematic of a cable terminal portion attached to a gear slider, according to some embodiments of the invention;

FIG. 11 is a simplified sectional view of a surgical mechanical arm actuator, according to some embodiments of the invention;

FIG. 12 is a flow chart of a method of manufacture of a mechanical articulated arm, according to some embodiments of the invention;

FIG. 13 is a flow chart of a detailed method of manufacture of an articulated surgical arm, according to some embodiments of the invention;

FIG. 14A is a simplified schematic of a portion of a surgical mechanical arm, according to some embodiments of the invention;

FIG. 14B is a simplified schematic of a distal portion of a surgical mechanical arm including a tool and a wrist bearing, according to some embodiments of the invention;

FIG. 14C is a simplified schematic of a wrist bearing, according to some embodiments of the invention; and FIG. 14D is a simplified schematic cross section of a shoulder bearing, according to some embodiments of the invention.

DESCRIPTION OF SPECIFIC EMBODIMENTS OF THE INVENTION

The present invention, in some embodiments thereof, relates to an articulated mechanical arm, robust and accurate mechanical control of the arm and, more particularly, but not exclusively, to an articulated mechanical arm which maintains its mechanical integrity under repetitive movement.

Overview

A broad aspect of some embodiments of the invention relates to support of one or more control cable of an articulated arm. In some embodiments, cable/s are maintained in known positions, potentially improving accuracy of control of the articulated arm by the cable/s. In some embodiments, a large proportion of a length of a control cable is supported, for example, at separated supports. A potential advantage being friction wear (e.g. associated with movement of the arm causing movement of cables within supports) being distributed over a large portion of the cable, potentially increasing lifetime of the cable. A further potential advantage being increased accuracy of control using the cable. For example, supporting a large proportion of the cable potentially means that tension on the cable/s is accurately transferred, for example, as changes in cable length in comparison to the long axis length of the arm when the cable is bent, tension is reduced by increasing the proportion of the cable which is supported. In some embodiments, 70-99.9%, or 80-99.9%, or 90-99.9%, or 90-99% or 93-97%, or about 95%, or lower or higher or intermediate ranges or percentages of a length of a control cable are supported.

In some embodiments, for a cable extending through a tubular portion including open spaces ("portion") (where, in some embodiments, open spaces enable bending e.g. as described below), 10-70%, 30-70%, or 20-50%, or 30-50%, or lower or higher or intermediate ranges or percentages, of a length of the cable extending through the portion is disposed within walls of the portion (e.g. bendable portion or flexible portion) where the remainder of the length of the cable is disposed within the open spaces.

In some embodiments, control cable/s control bending of the arm at one or more articulation. In some embodiments, bending is controlled by changing tension on one or more control cable. In some embodiments, one or more control cable actuates at least a portion of the articulated arm by torque applied to the control cable.

A broad aspect of some embodiments of the invention relates to an articulated arm including a tubular structure, where one or more control cable is located within a hollow passageway within a wall of the tubular structure. Potentially, locating a cable within the tubular structure wall means that a large proportion of the control cable is supported. Potentially, supporting a cable within a channel mechanically simplifies support of the cable e.g. in comparison to supporting the cable by coupling it to a tubular structure using additional element/s. Potentially, supporting a cable within a channel increases the strength of the cable support, potentially increasing robustness of the arm under loading, where loading, for example, in some embodiments, includes forces on the arm when a tool attaches (e.g. clamps down on tissue) and the arm is used to manipulate the tissue. An aspect of some embodiments of the invention relates to an articulated arm including at least two tubular structures where the tubular structures are nested within each other and where a control cable is located within a hollow passageway within a wall of the outermost tubular structure. A potential benefit being (e.g. as compared with control cable/s housed between an inner wall of the outermost tubular structure and an outer wall of the inner tubular structure) the ability, for given outer tubular structure outer cross sectional dimensions, to have thicker tubular structure walls. Additional benefits, include, for example, support of a large proportion of the control cable distributing friction wear along the control cable and/or maintaining of position of the control cable potentially contributing to more accurate control.

In some embodiments, the outermost tubular structure includes more than one hollow passageway, each hollow passageway housing at least one control cable. In some embodiments, the inner tubular structure includes one or more hollow passageway, each hollow passageway housing at least one control cable. In some embodiments, the hollow passageways are aligned circumferentially on the tubular structure.

In some embodiments, the articulated arm includes more than two nested tubular structures. For example, in some embodiments, a first tubular structure houses a second tubular structure and, optionally, in some embodiments, a third tubular structure is housed within the second tubular structure. In some embodiments, one or more of the tubular structures includes one or more cable passageways with a wall of the tubular structure, where the cable passageway houses control cable/s. In some embodiments, the articulated arm includes 2 or, 3 or, 4 or, 5 or, 2-5 or, 2-10 or lower or higher or intermediate numbers or ranges of nested tubular structures.

In some embodiments, an arm tubular structure includes one or more bendable portion and/or one or more flexible portion where bending of the arm at the flexible portion/s and/or bendable portion/s is controlled by changing tension on one of more control cables. In some embodiments, a bendable portion includes annular portions connected by connectors, where the control cables run through hollow passageways within annular portions and/or connectors. In some embodiments, a flexible portion includes a plurality of sequentially coupled links where, in some embodiments, control cable/s run through hollow passageways within the links.

An aspect of some embodiments of the invention relates to a tubular structure including a bendable torque transfer portion including a plurality of portions sequentially connected by connectors, where at least a portion of connectors connecting adjacent portions include channels configured to carry control cables. In some embodiments, one or more of the channels (which, in some embodiments, are hollow passageways) are disposed within walls of the tubular structure. In some embodiments, each portion includes one or more beams where beams are separated by spaces and connected by connectors. In some embodiments, the bendable torque transfer portion bends by bending of beams. Where, in some embodiments, beams bend towards each other on one side of the bendable torque transfer portion, reducing a space between the beams. In some embodiments, the beams carry the bending load. A potential advantage of disposing the control cables within the connectors is that the hollow passageway for the control cable is not located on a beam and does not weaken the beam. In some embodiments, disposing control cables within connectors increases a proportion of the cable which is supported, potentially reducing wear on the cable and/or increasing accuracy of control with the cable.

An aspect of some embodiments of the invention relates to an articulated arm including at least one tubular structure including a covered trench within a wall of the tubular structure, where covered trench is not integrally formed with the tubular structure. In some embodiments, the trench is sized and/or shaped to house one or more control cable. In some embodiments, the cover is recessed underneath an outer contour of the tubular structure.

In some embodiments, the tubular structure is constructed by cutting one or more trench in a tube, attaching a cover to the tubular structure, the cover covering at least an axial portion of the trench. In some embodiments, the tube is then cut to create flexible and/or bendable torque transfer portions (e.g. laser cut). In some embodiments, the cover includes a body portion and one or more wider end portions, where, in some embodiments the end portions are larger in a dimension perpendicular to a long axis of the body portion. Potentially, wider end portions strengthen coupling of the cover to the tube. In some embodiments, the cover is sized so that the end portions are located outside regions of flexible and/or bendable torque transfer portions, a potential benefit being stronger coupling without the welding region extending laterally at regions of the flexible and/or bendable portions.

An aspect of some embodiments of the invention relates to a shaped support structure configured to support and/or protect one or more cables disposed within an articulated arm tubular structure hollow passageway.

In some embodiments, the support structure rotates with an end effector of the articulated arm. In some embodiments, rotation of the end effector is actuated by rotation of a tubular structure coupled to the end effector. In some embodiments, the support structure is disposed with a central hollow passageway of the tubular structure and coupled to the support structure so that rotation of the tubular structure rotates the support structure. In some embodiments, the support structure is sized and/or shaped so that friction between the support structure and inner walls of the tubular structure is high enough that the support structure rotates with the tubular structure e.g. without addition coupling of the structures. For example, in some embodiments, the support structure contacts the inner wall of the tubular structure, for example, for 1-50%, or 5-30%, or 15-25%, or about 20% of the inner wall circumference cross section.

In some embodiments, the support structure supports a control cable, maintaining the control cable in a known position (and/or at a small distance from a known position), potentially increasing accuracy of control with the supported control cable.

In some embodiments, the support structure includes a hollow passageway in which an end effector actuation cable is disposed. In some embodiments, the support structure hollow passageway is configured (e.g. sized and/or shaped and/or has sufficiently low friction walls) that movement of the actuation cable does not generate movement in the support structure. In an exemplary embodiment, the end effector actuation cable actuates the end effector by torque.

In some embodiments, more than one cable is disposed in the hollow passageway within the tubular structure. For example, in some embodiments, the support structure holds more than one cable while separating the cables, potentially, reducing and/or eliminating friction between the cables e.g. during movement of the arm e.g. rotation of portion/s of the arm and/or bending at articulation/s.

In some embodiments, a second cable is disposed within the hollow passageway of the tubular structure where the support structure and/or tubular structure are configured so that their rotation rotates the second cable. In some embodiments, the second cable is disposed between an outer surface of the support structure and an inner wall of the tubular structure. In some embodiments, more than two cables are disposed within the hollow passageway, for example, more than one inelastic cable (e.g. power supply cable), for example, more than one control cable.

In some embodiments, the support structure includes a trench sized and/or shaped to receive the second cable. In some embodiments, the second cable is held in position between the trench and the inner walls of the tubular structure.

In some embodiments, the support structure continuously supports 80-99.9%, or 90-99.9%, or 90-99%, or 90-95% of a length of one or more cable.

In some embodiments, the second cable has limited elasticity (e.g. an electrical supply cable). In some embodiments, the support structure is shaped to provide support to a cable while guiding the cable along a path which is distributed around a circumference of the support, for example, a helical path around the support structure. In some embodiments, the support structure holds the cable while allowing axial movement of the cable on the support e.g. during bending of the support, where, for example, in some embodiments, the cable disposed on the inside of the bend slides towards the cable disposed on the outside of the bend.

An aspect of some embodiments of the invention relates to actuator parts configured for case of correct manufacture of an actuator for a surgical mechanical arm. In some embodiments, slider/s actuating control cable/s configured to move linearly on a shaft (e.g. by threading) have different size and/or shape (e.g. different sector angles and/or thicknesses) so that a hollow configured to receive each slider has a different size and/or shape, potentially ensuring correct placing of the sliders within the hollow.

In some embodiments, actuation of flexion of a surgical mechanical arm flexible portion is controlled by changing tension on one or more cables coupled to the flexible portion. In some embodiments, control cable tension (for one or more cables) is controlled by linear movement of a slider coupled to a shaft where rotation of the shaft generates linear movement of the slider (e.g. via threading on the shaft and/or slider). In an exemplary embodiment, a first and second slider are coupled to the shaft and the sliders control flexion of a surgical mechanical arm flexible portion, the sliders moving linearly in opposite directions with rotation of the shaft, a first cable coupled to one slider relaxing and a second cable coupled to the other slider tensioning to bend the flexible portion.

An aspect of some embodiments of the invention relates to incorporation of an additional length of a cable (e.g. electrical supply cable) into an articulated arm. In some embodiments, an additional length of cable is located at a portion of the arm; additional, for example, in some embodiments, refers to a length of cable not required to have the cable extend along a length between two connections of the cable to the arm. In some embodiments, the additional length is released, for example, to provide additional length so that a portion of the cable may be removed. In some embodiments, the cable is wound around one or more portions of the articulated portion such that the cable may be unwound to increase a length of the cable. In some embodiments, the additional portion of cable is covered by a cover. Potentially, an additional cable enables repair and/or maintenance and/or change in configuration of the cable and/or connection/s of the cable.

In an exemplary embodiment, an electrical supply cable includes an additional length of cable disposed at a proximal end of the electrical supply cable. In some embodiments, an electrical supply cable extends along at least a portion of a length of the arm, towards an electrosurgical tool at a distal portion of the arm e.g. at a distal end of the arm. In some embodiments, the electrical supply cable transfers electrical power from an electrical contact at a proximal end of the arm to the electrosurgical tool. In some embodiments, the electrosurgical tool is rotatable (e.g. about a long axis of the articulated arm), in some embodiments, the electrical supply cable rotates with the electrosurgical tool. In an exemplary embodiment, the electrical supply cable is wound around a rotatable shaft by which the cable is supported, and unwound to release an additional cable length.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

In some embodiments, one or more tubular structure is constructed from stainless steel. Alternatively or additionally, in some embodiments, one or more tubular structure is constructed from plastic. In some embodiments, the surgical mechanical arms are disposable single-use surgical instruments. Alternatively, in some embodiments, portion/s of the surgical mechanical arm are sterilized by autoclave and/or ETO sterilization (ethylene oxide sterilization). In some embodiments, the surgical mechanical arm is dismantled partially or entirely before sterilization.

Exemplary Articulated Mechanical Arm

Figure 1:
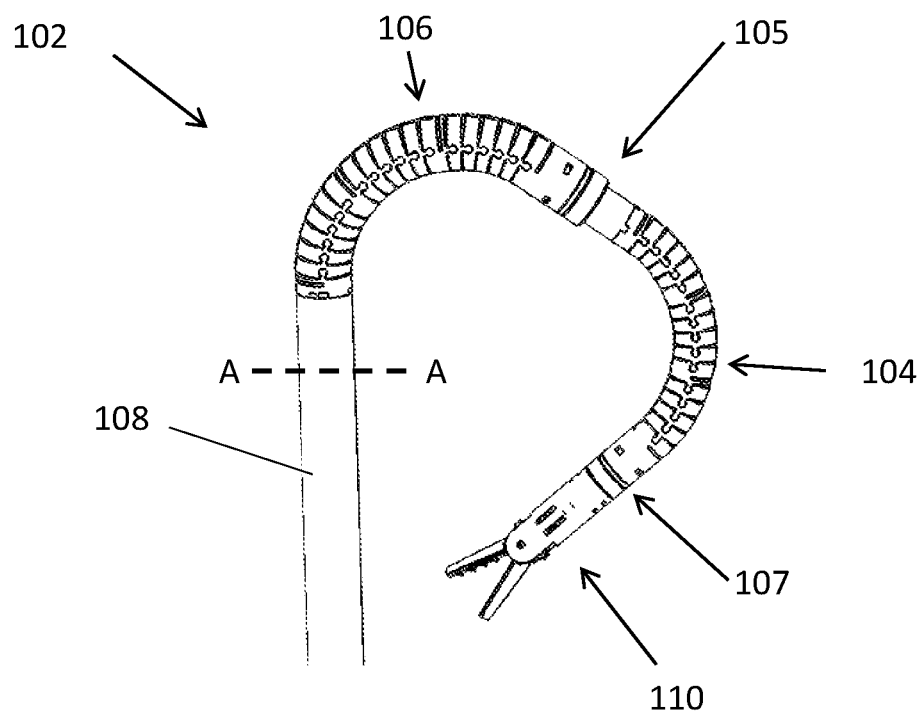
FIG. 1 is a simplified schematic side view of a mechanical arm, according to some embodiments of the invention.

FIG. 1 is a simplified schematic side view of a mechanical arm 102, according to some embodiments of the invention.

In some embodiments, mechanical arm 102 includes a plurality of articulations; flexible portions 104, 106. In some embodiments, the mechanical arm includes one or more rigid portions (e.g. one or more of portions 105, 107, 108 are rigid) articulations alternate with rigid portions. In some embodiments, bending at one or more of the flexible portions is where bending is distributed along a length of the flexible portion.

In some embodiments, mechanical arm 102 includes a first flexible portion 104 coupled to a second flexible portion 106. In some embodiments, the second flexible portion is coupled to a rigid support portion 108. In some embodiments, the first flexible portion is coupled to an end effector 110.

In some embodiments, one or both flexible portions 104, 106 are bendable, each portion in a single bending plane. In some embodiments, each flexible portion is bendable in a single bending plane in one rotational direction from a straight configuration.

In some embodiments, one or both flexible portions 104, 106 are rotatable about a flexible portion long axis. Rotation of the second flexible portion 106 thereby changes the orientation of the single bending plane of the first flexible portion 104. In some embodiments, rotation of a flexible portion is effected by rotation of a rigid portion coupled to the flexible portion. For example, in some embodiments, the second flexible portion 106 is rotated about the second flexible portion long axis by rotation of support portion 108 about a support portion long axis.

In some embodiments, mechanical arm 102 is a surgical mechanical arm, for example, sized and/or shaped for insertion into a body (e.g. human body). For example, in some embodiments, the surgical mechanical arm is sized and/or shaped for laparoscopic surgery and/or for insertion through a natural orifice and/or lumen e.g. vagina, anus, mouth, trachea, esophagus, or ear canal. In some embodiments, a maximum cross sectional dimension of the arm and/or of a distal portion of the arm is 0.5-20 mm, or 1-10 mm, or 1-5 mm, or lower or higher or intermediate ranges or dimensions. Where the distal portion is defined as a distal 5-90%, or 5-50%, or 5-20%, or lower or higher or intermediate percentages or ranges of a long axis length of the mechanical arm and/or is defined as a portion of the arm distal of and including the second flexible portion 106.

Figure 2:
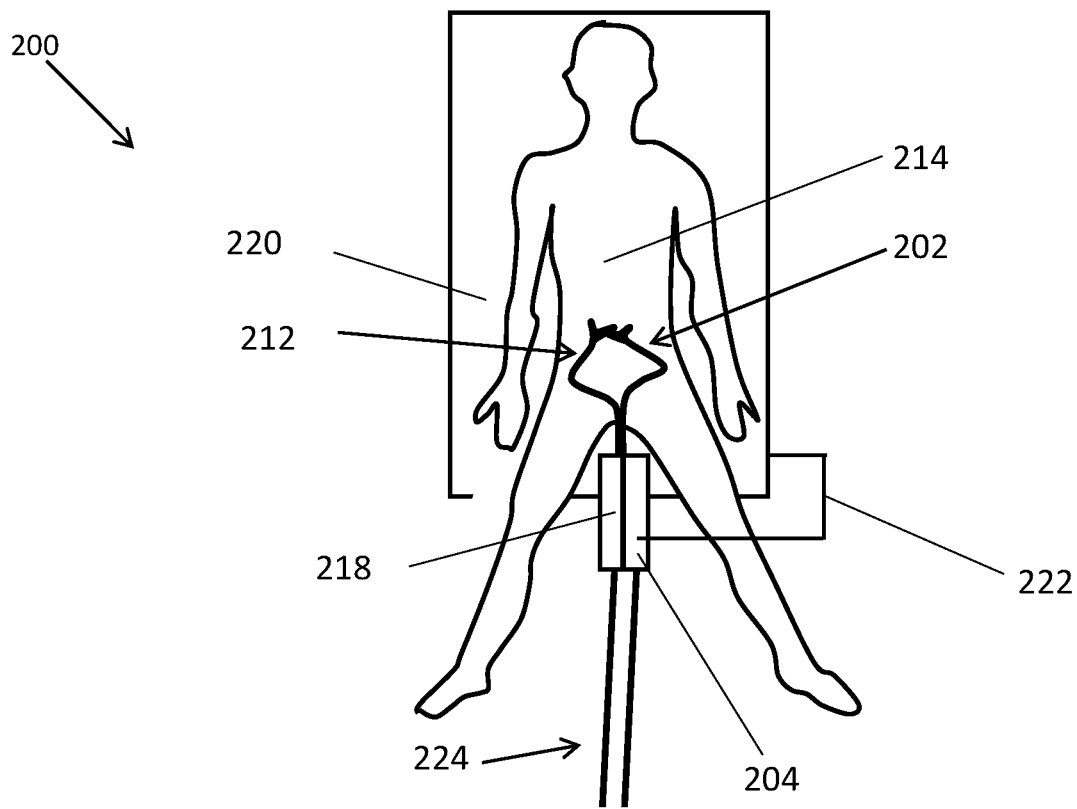
FIG. 2 is a simplified schematic of a surgical system, according to some embodiments of the invention.

FIG. 2 is a simplified schematic of a surgical system 200, according to some embodiments of the invention.

In some embodiments, system 200 includes one or more surgical arm, for example, two surgical arms 202, 212. In some embodiments, each surgical arm is actuated by a motor unit 218, 204. In some embodiments, motor units 218, 204 are connected to each other. In some embodiments, one or both motor units 218, 222 are supported by a support 222. In some embodiments, support 222 is connected to a patient support 220 (e.g. surgical bed).

In some embodiments, surgical arms 202, 212, are inserted into a patient 214 e.g. through a natural orifice (e.g. through the vagina). In some embodiments, motor units 204, 218, receive electrical power and/or control instructions through cables 224.

FIGS. 3A-B are simplified schematics of a mechanical arm 302, according to some embodiments of the invention.

In some embodiments, a surgical mechanical arm 302 including flexible portion/s (e.g. including one or more feature as described and/or illustrated regarding surgical arm 102 and/or flexible portions 104, 106, FIG. 1) includes one or more nested tubular structures.

In some embodiments, a portion is rotated about a portion's long axis and/or a surgical mechanical arm's long axis by rotation of a portion distal to and connected to the portion (e.g. including one or more feature as described regarding the second flexible portion 106 and support portion 108 FIG. 1). Additionally or alternatively, in some embodiments, a portion is rotated by rotation of a proximal end of the portion.

In some embodiments, FIGS. 3A-B illustrate rotation of a distal end 330 of mechanical arm 302 by rotation of a proximal portion 332 proximal to and coupled to distal end 330. In some embodiments, distal end 330 includes an end effector and/or connector for an end effector 310.

FIG. 3B illustrates embodiments where proximal portion 332 includes one or more flexible torque transfer portion, which is, for example, configured to transfer torque applied to one end of the torque transfer portion to another where one or more torque transfer portions include one or more features as illustrated and/or described regarding 638 FIGS. 6A-E.

In some embodiments, distal end 330 and proximal portion 332 are a tubular structure. In some embodiments, mechanical arm 302 includes a plurality of tubular structures, for example, in an exemplary embodiment, three tubular structures, an inner tubular structure 324, an intermediate tubular structure 326 and an outer tubular structure 328. Where, in some embodiments, each tubular structure includes one or more flexible portion and/or one or more flexible torque transfer portions.

Exemplary Arm Including Exemplary Control Cable Housing

FIGS. 4A-B are simplified schematic cross sections of a mechanical arm 402, according to some embodiments of the invention.

In some embodiments, mechanical arm 402 includes a first and a second flexible portion 404, 406 respectively. In some embodiments, flexible portions 404, 406 include one or more feature as described and/or illustrated regarding flexible portions 104, 106 FIG. 1.

In some embodiments, mechanical arm 402 includes one or more nested tubular structures. In some embodiments, the mechanical arm includes an inner tubular structure 424, an intermediate tubular structure 426 and an outer tubular structure 428.

In some embodiments, one or more tubular structure includes a flexible portion and/or a torque transfer portion where, in some embodiments, in FIGS. 4A-B, dotted fill indicates a torque transfer portion and angled shading indicates a flexible portion where one or more torque transfer portion includes one or more features as illustrated and/or described regarding 638 FIGS. 6A-E.

In some embodiments, inner tubular structure 424 includes a first and a second torque transfer portion 434, 436, respectively.

In some embodiments, intermediate tubular structure 426 includes a torque transfer portion 438 and a first flexible portion 404.

In some embodiments, outer tubular structure 428 includes a second flexible portion 406.

In some embodiments, flexion of one or more of flexible portions 404, 406 is controlled by changing the tension on one or more element coupled to a portion of the surgical mechanical arm.

For example, in some embodiments, FIGS. 4A-B illustrate flexion of first flexible portion 404 controlled by one or both of first flexible portion cables 444, 446. Movement from the configuration illustrated in FIG. 4A to that illustrated in FIG. 4B effected, for example, by pushing on cable 444 and/or pulling on cable 446.

Similarly, in some embodiments, flexion of second flexible portion 406 is controlled by one or both of second flexible portion cables 448, 450.

In some embodiments, one or more flexible portions are each controlled by more than two cables, for example, 3-15, or 3-10, or 3-6 cables, or lower or higher or intermediate numbers or ranges of cables. In some embodiments, one or more flexible portions are each controlled by a single cable.

In some embodiments, one or more cables run through a hollow passageway within a solid portion of the mechanical arm. For example, in some embodiments, a cable runs through a hollow passageway within a tubular portion.

In an exemplary embodiment, cable/s configured to control a flexible portion run through hollow passageway/s within a tubular structure of which the flexible portion is a part. For example, in some embodiments, control cables 448, 450, each run through a hollow passageway within the tubular structure.

In some embodiments, a distal portion of arm 402 e.g. a distal portion of inner tubular structure 424 is rotatable by rotation of a proximal portion of the inner tubular structure.

In some embodiments, first flexible portion cables 444, 446 are connected to intermediate tubular structure 426 at connections 452, 454 respectively. In some embodiments, second flexible portion cables 448, 450 are connected to outer tubular structure 428 at connections 456, 458 respectively.

In some embodiments, connection of one or more control cables to a tubular structure is by connecting a distal portion (e.g. end) of the cable/s to the tubular structure e.g. by welding.

In some embodiments, one or more control cable is a tape shaped cable, for example, having a cross section with an aspect ratio of larger than 1:1, for example 1:1.1, or 1:1.5, or 1:2, or 1:1.1-1:2, or lower or higher or intermediate ranges or ratios. Potential advantages of a tape shaped cable include strength and/or resistance to rotation and/or twisting. In some embodiments, one or more control cable is a braided cable, a potential advantage being flexibility of the cable. In some embodiments, one or more control cable is coated, for example, with a low friction coating (e.g. plastic coating) potentially reducing friction between the cable and other portion/s of the mechanical arm (e.g. trench), potentially reducing wear on the cable.

In some embodiments, one or more (e.g. all) tubular structure is rigid between flexible portions and/or proximally of distal portions.

In some embodiments, end effector 410 is actuated by rotation of element/s coupled to the end effector. In some embodiments, actuation of an end effector by rotation includes one or more features as described and/or illustrated regarding FIGS. 36A-B of International Patent Application No. WO2016/035084 and/or FIGS. 11A-C and 12A-B of U.S. patent application No. 62/583,543, which applications are incorporated by reference in their entireties.

Alternatively or additionally, in some embodiments, end effector 410 is actuated by changing the tension on one or more control cables e.g. by "push-pull" where actuation is effected by tensioning one or more control cable while relaxing other control cable/s.

In some embodiments, one or more tubular structures are each coupled to another tubular structure (e.g. a tubular structure is coupled to a structure surrounding it). For example, in some embodiments, outer tubular structure 428 is coupled to intermediate tubular structure 426 by connector 470. For example, in some embodiments, intermediate tubular structure 426 is coupled to inner tubular structure 424 by connector 472. In some embodiments, one or more of connectors 470, 472 prevent axial movement of the tubular structures with respect to each other. Additionally or alternatively, in some embodiments, one or more of connectors 470, 472, include bearings which facilitate rotation of tubular structures (e.g. each tubular structure about its long axis and/or about a long axis of the arm) with respect to each other.

FIG. 5A is a simplified schematic section view of a mechanical arm 500, according to some embodiments of the invention. In some embodiments, one or more cable (e.g. control cable) is housed in a channel within a wall of a tubular structure. In some embodiments, channel/s are formed by a trench within the tubular structure wall which is, in some embodiments, covered, at least partially with cover/s.

In some embodiments, FIG. 5A illustrates a section taken of the mechanical arm of FIG. 1 along the dashed line labeled AA and/or of the mechanical arm of FIG. 4A along the dashed line labeled BB.

Visible in FIG. 5A are an outer tubular structure 528, an intermediate tubular structure 526 and an inner tubular structure 524. In some embodiments, one or more tubular structures 524, 526, 528, each include one or more trenches 560, 562, 564, 566. In some embodiments, one or more tubular structures each include two trenches, which are, in some embodiments, disposed opposite each other e.g. symmetrically placed with respect to the center of the tubular structure. In some embodiments, outer tubular structure 528 includes outer tubular structure trenches 560, 562. In some embodiments, intermediate tubular structure 526 includes intermediate tubular structure trenches 564, 566.

In some embodiments, one or more trenches each house one or more control cables. In an exemplary embodiment, each trench houses a single control cable, where, in some embodiments, trenches 560, 562, 564, 566 house cables 568, 570, 572, 574 respectively.

In some embodiments, one or more trenches (e.g. each trench) are at least partially enclosed by one or more covers where, in an exemplary embodiment, trenches 560, 562, 564, 566 are covered by covers 584, 586, 588, 590 respectively.

In some embodiments, a cross sectional shape of one or more axial portions of one or more trench (e.g. one or more of trenches 564, 566, 560, 562) is a circular segment, for example, a semi-circular shape. In some embodiments, a trench has a constant cross-sectional shape (where the cross section is taken perpendicular to a long axis of the trench).

Figure 5B:
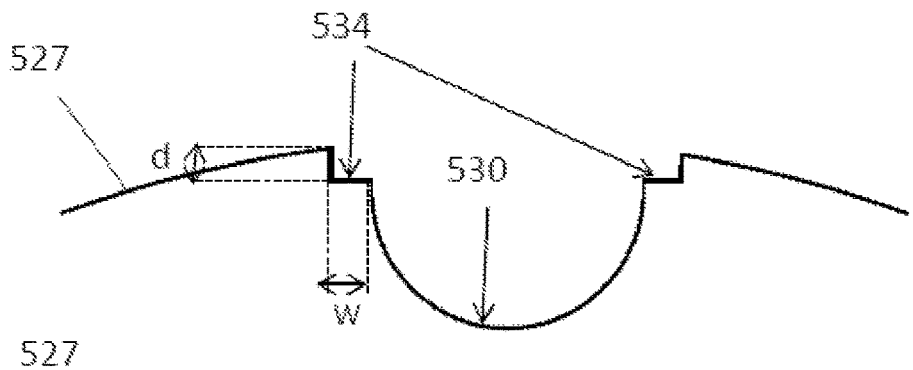
Figure 5C:
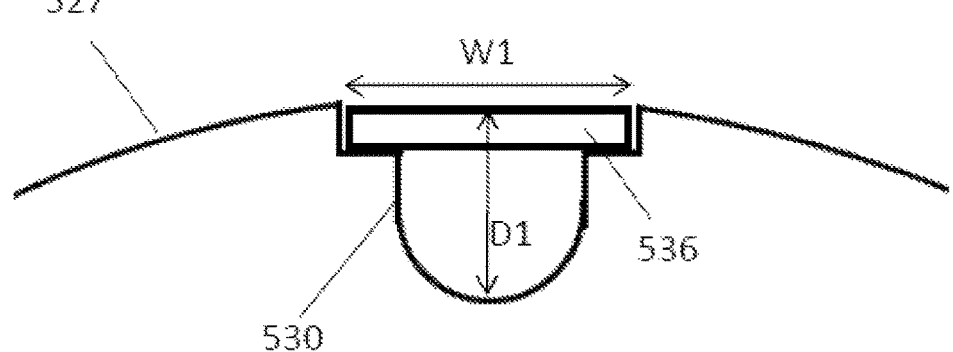
Figure 5D:
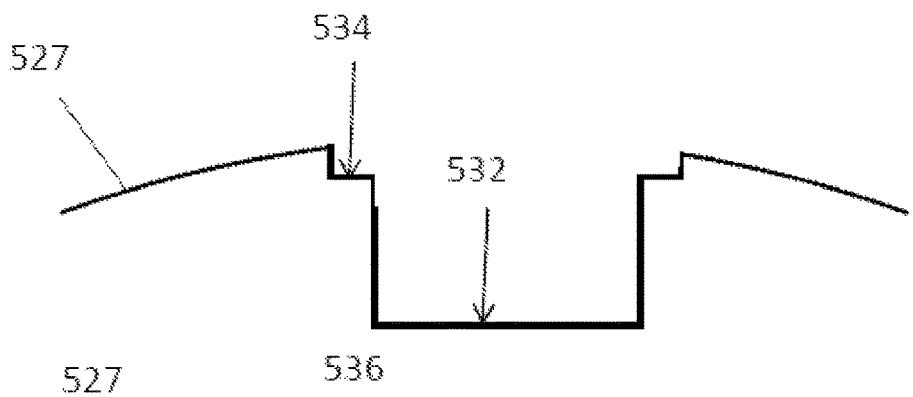

In some embodiments, a trench includes one or more flange (e.g. including one or more feature as illustrated and/or described regarding FIG. 5B and/or FIG. 5D) and the cover contacts and/or is attached to the flange.

Figure 5E:
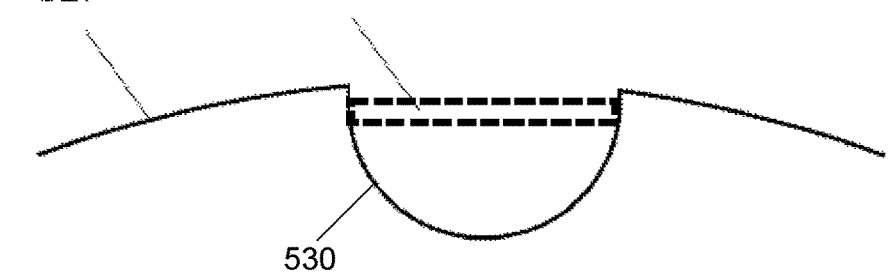
Figure 5F:
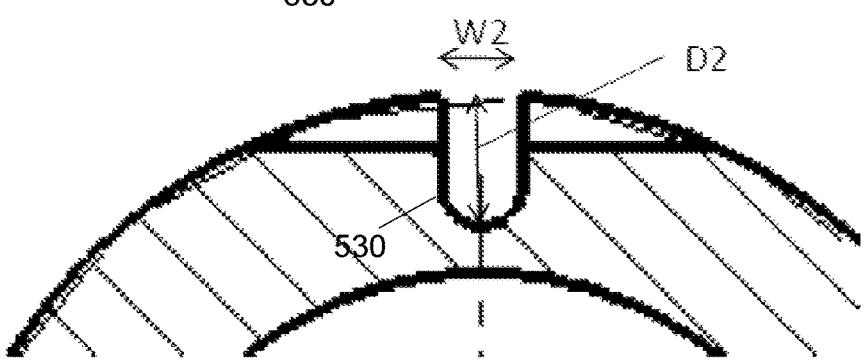

In some embodiments, a trench lacks flanges, the cover, for example, contacting and/or connected to walls of the trench e.g. including one or more feature as described and/or illustrated regarding FIG. 5E.

In some embodiments, surgical mechanical arm 500 has trenches with different shapes and/or dimensions. For example, in some embodiments, the mechanical arm has different sized and/or shaped trenches, for example, the trenches configured for compatibility with dimension/s of the tubular structure of which they are a part and/or to accommodate different numbers and/or sizes and/or shapes of cable disposed within the trench.

For example, in some embodiments, trenches of intermediate tubular structure 526 and trenches of outer tubular structure 528 have different shape and/or dimensions.

In an exemplary embodiment, intermediate tubular structure trenches 564, 566 lack continuous flanges, where, for example, over 90%, or over 95% or lower or higher or intermediate percentages, of a length of the trench lacks flanges, e.g. including one or more feature as illustrated and/or described regarding FIG. 5E.

In an exemplary embodiment, intermediate tubular structure trenches 564, 566 have a semi-circular cross-sectional shape where the circle diameter is 0.4 mm.

In an exemplary embodiment, outer tubular structure trenches 560, 562, have flanges for over 70%, or over 80%, or over 90% or over 95%, or lower or higher or intermediate percentages, of a length of the trench.

In an exemplary embodiment, intermediate tubular structure trenches 560, 562 have a semi-circular cross-sectional shape where the circle diameter is 0.6 mm.

FIGS. 5B-F are simplified schematic cross sections of tubular structure trenches, according to some embodiments of the invention. In FIGS. 5B-5E, the tubular structure outer wall is denoted as 527.

In some embodiments, FIG. 5C illustrates a trench after attachment of a cover 536 where, in some embodiments, a width of a trench is measured as the largest dimension of the trench cross section in a direction perpendicular to a tubular structure radial direction where, in some embodiments, depth of a trench is measured as the largest dimension of the trench cross section in the tubular structure radial direction. In some embodiments, trench cross sectional dimensions are constant along a length of the tubular structure. Alternatively, in some embodiments, trench cross section changes (e.g. tapers) along a tubular structure length.

In some embodiments, one or more covers and/or trenches are sized and/or shaped so that the cover does not protrude from an outer contour of the tubular structure, e.g. the cover is recessed within the trench where the outer contour, for example, in some embodiments, is a smooth curve surrounding the tubular structure which contour has, in some embodiments, a circular cross section.

In some embodiments, the cover is recessed within the outer contour by resting on a flange e.g. as illustrated in FIGS. 5B-D. In some embodiments, the cover is recessed by resting (e.g. being attached) on walls of the trench, for example, as illustrated in FIG. 5E.

In some embodiments, a mechanical arm includes an intermediate tubular structure (e.g. 426 FIG. 4B) which includes trenches which lacks flanges. In some embodiments, a mechanical arm includes an outer tubular structure (e.g. 428 FIG. 4B) which includes trenches with flanges.

Alternatively, in some embodiments, all trenches of a mechanical arm include flanges. Alternatively, in some embodiments, all trenches of a mechanical arm lack flanges. In some embodiments, a single tubular structure includes a trench with a flange and/or with portions which include a flange and a trench lacking a flange.

Referring now to FIGS. 5B-D, in some embodiments, a trench has one or more flange 534 sized and/or shaped to support edge/s of cover 536, shown for example in FIGS. 5C, 5E.

In some embodiments, one or more trench of the outer tubular structure (e.g. both trenches of a two trench outer tubular structure) include a trench which, in an exemplary embodiment, is about 0.6 mm deep and wide e.g. has a semicircular cross-section where the diameter of the semicircle is about 0.6 mm. In some embodiments, trench depth (and/or diameter) is 0.1-2 mm, or 0.2-1 mm, or lower or higher or intermediate ranges or distances.

In some embodiments, one or more trench of the outer tubular structure (e.g. both trenches of a two trench outer tubular structure) include a flange which, in an exemplary embodiment, has a depth of about 0.15 mm and a width of about 0.2 mm (e.g. depth d, width w, referring to FIG. 5B). In some embodiments, flange width and/or depth is 0.01-1 mm, 0.05-0.5 mm, or 0.1-0.3 mm, or lower or higher or intermediate ranges or distances.

In some embodiments, one or more trench of the intermediate tubular structure (e.g. both trenches of a two trench intermediate tubular structure) include a trench which, in an exemplary embodiment, is about 0.4 mm deep and about 0.7 mm wide where a base of the trench has a rounded base, with e.g. a semicircular cross-section where the diameter of the semicircle is about 0.4 mm. In some embodiments, intermediate tubular structure trench/es are 0.05-1 mm wide (e.g. width W2 FIG. 5F), or 0.2-0.6 mm wide or lower or higher or intermediate ranges or widths. In some embodiments, intermediate tubular structure trench/es are 0.05-2 mm deep (e.g. depth D2 FIG. 5F), or 0.2-1 mm deep or lower or higher or intermediate ranges or depths.

In some embodiments, a cross section of a trench 530 has a rounded shape (e.g. as illustrated in FIGS. 5B-C, E-F). For example, semi-circular. Alternatively, in some embodiments, e.g. as illustrated in FIG. 5D, a trench 532 has non rounded cross-sectional shape, for example including one or more corners with an angle of 20-260°, or 45-135° or lower or higher or intermediate angles or ranges.

FIG. 6A is a simplified schematic of a tubular structure 600, prior to laser cutting, according to some embodiments of the invention.

FIG. 6B is a simplified schematic of a tubular structure 601, after laser cutting, according to some embodiments of the invention.

FIG. 6C is an enlarged portion of FIG. 6B, according to some embodiments of the invention.

In some embodiments, tubular structure 600 is laser cut to produce tubular structure 601. Alternatively or additionally, in some embodiments, cutting by another technique e.g. water jet and/or plasma jet cutting.

In some embodiments, tubular structure 600 includes one or more trench which, in some embodiments is oriented parallel to a long axis of tubular structure 600. In some embodiments, one or more trench is covered by one or more cover 688, 690. In some embodiments one or more cover (e.g. of covers 688, 690) are not an integral part of the tubular structure. In some embodiments, one or more of covers 688 is attached (e.g. welded, e.g. laser welded) to the tubular structure where attachment, for example, includes attachment to surface/s within the trench/s. In some embodiments, when tubular structure 600 is cut to create tubular structure 601, covers 690, 688 are cut into sections 682, 680 respectively.

In some embodiments, the trench and/or channel made by covering the trench is configured to carry one or more cable, e.g. a control cable 644 which is visible in FIG. 6B in the spaces cut through the tubular section of FIG. 6A and portion/s of the trench not covered by the covers.

In some embodiments, FIG. 6B illustrates a portion of an intermediate tubular structure, which, for example, includes one or more features as described and/or illustrated regarding intermediate tubular structure 426 FIGS. 4A-B. In some embodiments, tubular structure 601 includes a flexible portion 604 and a torque transfer portion 638 where flexible portion 604, in some embodiments, includes one or more features as illustrated in and/or described regarding "flexible portions" and where torque transfer portion 638 includes one or more feature as illustrated and/or described regarding torque "transfer portions" in International Patent Application No. WO2016/035084.

In some embodiments, the tubular structure includes a portion 676 configured for coupling the tubular structure to an external tubular structure (e.g. outer tubular structure 428 FIGS. 4A-B). In some embodiments, portion 676 includes an annular trench 678 which is sized and/or shaped to receive a portion of a connector (e.g. connector 470 FIGS. 4A-B) potentially preventing axial movement between the connector and tubular structure e.g. whilst allowing rotation of the tubular structure within the connector, for example, where the connection is a bearing. In some embodiments, portion 676 does not include a cover for the cable trench, potentially reducing friction between tubular structure 601 and a connector aligned with portion 676.

In some embodiments, one or more of covers 690, 688 includes one or more portion 603, 689, having a larger width than a body and/or an average width of a body of the cover. In some embodiments, a cover includes end portions which are wider than a central body of the cover.

For example, referring now to FIG. 6C, in some embodiments a width 605 of a wider portion (e.g. end portion) of the cover is, for example, 1.1-10 times, or 1.1-3, or 1.1-2 times or about 1.5 times, or lower or higher or intermediate multiples or ranges of a width 607 of a body of a cover and/or of an average width of a body of the cover. In an exemplary embodiment, width 605 is about 0.9 mm, width 607 is about 0.6 mm and length 615 is about 0.4 mm.

In an exemplary embodiment, a cover includes a wider end portion for both ends e.g. as illustrated in FIG. 6E. In some embodiments, a cover includes more than two wider portions, for example, 3-5, for example, the wider portions distributed along a length of the cover.

Potentially, the cover's wider portion/s facilitate positioning of the cover and/or increase the strength of coupling of the cover to the tubular structure and/or trench. For example, in some embodiments, wider portion/s hold the cover to the trench securely during attachment of the cover e.g. by laser welding, potentially enabling a thinner trench and/or cover. In some embodiments, a thinner trench and/or cover enables a torque transfer portion with smaller struts (struts e.g. as described herein below), a potential advantage being increased elasticity of bending of the torque transfer portion. In some embodiments, increased elasticity of the torque transfer portion contributes to increased robustness of the portion under repeated bending movements of the portion.

In some embodiments, trench flanges are expanded outside area/s of the tubular structure's flexible portion/s and/or torque transfer portion/s, for example, inlets 692 and 609, FIG. 6B. In some embodiments, a width 611 (FIG. 6C) of an inlet 692 is 1.5-20 times or 2-10 times a width 605 of the end of the cover and/or of a body of the cover 607. In some embodiments, a height 613 (FIG. 6C) of an inlet 692 is 1.5-20 times or 2-10 times a height 615 of the end of the cover.

In some embodiments, the inlet is sufficiently deep to hold the cover without the cover protruding from a surface of the tubular structure. For example, the inlet being 1-2 or 1-1.5 times, or lower or higher or intermediate multiples or ranges of a thickness of the cover. In some embodiments, a longer indent than length 615 of the end portion enables attachment of a cover where there is a difference between a length of the cover and a length of the trench.

In some embodiments, for one or more bendable portion of the arm, bending of bendable portion 680 is by bending of beams 681 of a portion to reduce spaces 683 between the beams (e.g. including one or more features as described and/or illustrated regarding FIGS. 21-26 of International Patent Application No. WO2016/035086).

In some embodiments, for one or more bendable portions of the arm, a thickness of beam/s in an axial direction is 0.1-10%, or 1-10%, or 1-5%, or about 3% of the diameter of the tubular structure. In some embodiments, the thickness of spaces in the axial direction is within 20%, or 10%, or 5%, or 2% of the thickness of the beams.

In some embodiments, for one or more bendable portions of the arm, the thickness of beam/s in an axial direction is 20-90%, or 40-70%, or lower or higher or intermediate percentages or ranges of a thickness of a wall of the tubular structure.

In some embodiments, for one or more bendable portions of the arm, the thickness of the beam in an axial direction is 0.01-3%, or 0.5-2%, or about 1%, or lower or higher or intermediate range percentages of an axial length of the bendable portion.

Exemplary Torque Transfer Portion Structure

In some embodiments, torque transfer portion 638 includes one or more features as illustrated and/or described regarding torque transfer portions in International Patent Application No. WO2016/035084.

FIG. 6D is a simplified schematic of a portion of a torque transfer portion 638, according to some embodiments of the invention.

In some embodiments, FIG. 6D illustrates a portion of torque transfer portion 638 of FIG. 6B.

In some embodiments, torque transfer portion 638 includes a plurality of annular portions aligned into a tubular structure, where each annular portion is connected to adjacent annular portions by one or more strut. In an exemplary embodiment, each annular portion is connected to each adjacent annular portion by two struts. In some embodiments, struts are spaced equally circumferentially with respect to the annual portions.

In FIG. 6D, exemplary annular portions are indicated by dashed lines. Where a central annular portion 691 is connected to adjacent annular portions 693, 695 by struts 697 and 699 respectively. In some embodiments, each annular portion is connected to adjacent annular portions by two struts.

FIG. 6E is a simplified schematic plan view of a torque transfer portion 638, for example as shown in FIG. 6B, 6D, according to some embodiments of the invention.

Visible in FIG. 6E are the struts 697 and 699. FIG. 6E shows strut 671 connecting annular portion 691 to annular portion 693 and strut 671 connecting annular portion 691 to annular portion 695. In some embodiments, struts 671, 699 include trenches 664, 666 respectively (and in some embodiments, a cover to the trench) providing a hollow passageway configured to house a control cable.

Exemplary Cable Support Structure

In some embodiments, an articulated arm (e.g. including one or more feature as described and/or illustrated regarding FIGS. 1, 3A-B. 4A-B, 5A-E) includes an elongate support structure coupled to one or more cables disposed in a hollow passageway of a tubular structure. In some embodiments, the cable/s are disposed within a hollow passageway of an innermost tubular structure (e.g. innermost tubular structure 424 FIGS. 4A-B). In some embodiments, the support structure separates one or more cables, for example, preventing the cables from touching each other, for at least a portion of the length of the cables. In some embodiments, the support structure supports and/or guides one or more cables, for example, holding a cable in a known position e.g. with respect to other portion/s of the arm.

In an exemplary embodiment, an elongate support structure supports a single end effector control cable and a single electrosurgical supply cable (e.g. configured to supply monopolar and/or bipolar power).

For example, returning now to FIG. 5A, in some embodiments, a hollow passageway 576 within inner tubular structure 524 houses an end effector control element 578 and/or an end effector electrosurgical supply cable 580. In some embodiments, control element 578 and/or cable 580 are supported by a support structure 582. Where, in some portion/s of the arm control element 578 is a shaft and in some portion/s of the arm control element 578 is a cable e.g. a torque cable.

In some embodiments, end effector control element 578 (e.g. including, in some embodiments, a torque cable and/or a shaft) controls actuation of the end effector (e.g. end effector 110 FIG. 1, 410 FIGS. 4A-B) where, for example, in some embodiments, end effector control element 578 is configured to transfer torque to the end effector, which actuates the end effector, for example, opening and/or closing a gripper or scissors end effector. In some embodiments, control element 578 transfers torque applied by a motor e.g. located proximally of the end effector and/or at a proximal end of the articulated arm.

Alternatively or additionally, in some embodiments, the end effector is actuated by changing tension on one or more control cable coupled to the end effector (e.g. a by "push pull") e.g. including one or more feature as described and/or illustrated regarding tool actuation in US Patent No. U.S. Pat. No. 9,039,057 which is herein incorporated by reference in its entirety.

In some embodiments, the support structure is an elongate element. In some embodiments, the support structure supports (e.g. continuously supports) at least 20% or 40%, or 60%, or 80%, or lower or higher or intermediate percentages of a length of one or more cable disposed within a tubular structure (e.g. the innermost tubular structure).

In some embodiments, the support structure is sized and/or shaped so that cable/s supported by the support structure are in a known position within the hollow passageway, potentially improving accuracy of control using the cable/s, for example, when the control cable/s have a small cross section with respect to the cross section of the hollow passageway.

In some embodiments, a cross section of the support structure is sized and/or shaped to sit within the hollow passageway and to hold one or more cable at a radial position within the hollow passageway which varies by at most 1-20%, or 1-5% of the diameter of the hollow passageway.

FIG. 7A is a simplified schematic side view of an end effector 710 and a portion of an end effector support structure 712, according to some embodiments of the invention.

FIG. 7B is a simplified schematic view of a portion of an end effector 710, a support structure 712 and a sectional view of a tubular structure 714, according to some embodiments of the invention.

In some embodiments, tubular structure 714 is an innermost tubular structure of an articulated arm, e.g. including one or more features described and/or illustrated regarding inner tubular structure 424 FIGS. 4A-B. In some embodiments, a cable 780 extends throughout tubular structure 714, the cable being coupled to a support structure 712.

FIG. 7C is a simplified schematic view of cable 780 being coupled to the support structure 712, according to some embodiments of the invention.

In some embodiments, cable 780 is an electrical supply cable, for example, in some embodiments, configured to supply electrosurgical power. Alternatively, or additionally, in some embodiments, cable 780 and/or an additional cable is configured to carry data (e.g. from sensor/s, e.g. control signal/s) and/or provide power for other purposes e.g. for lighting, sensor power supply.

In some embodiments, support structure 712 is sized and/or shaped to accommodate cable/s within a hollow channel 724 within support structure 712. In some embodiments, a single control cable 725 is located within the hollow channel. In an exemplary embodiment, a torque transfer element 725 is located within the hollow channel. In some embodiments, the hollow channel is sized and/or shaped to allow torque transfer element 725 (which is e.g. in some embodiments, a torque cable) to rotate within the hollow channel.

In some embodiments, support structure 712 is sized and/or shaped to rotate when surrounding tubular structure 714 rotates. For example, in some embodiments, support structure 712 is sized and/or shaped to have high friction between the tubular structure and the support structure. In some embodiments, a maximum cross-sectional dimension of an outer contour of support structure 712 and an inner wall diameter of tubular structure 714 are the same or are within 0.5%, or 1% of the same dimension.

In some embodiments, contact between support structure 712 and inner walls of the surrounding tubular structure, for at least an axial portion of the arm is 5-50%, or 5-30%, or 5-20%, or 10-20%, or about 15%, or lower or higher or intermediate percentages or ranges of a surface of the inner wall of tubular structure 714. In some embodiments, the tubular structure inner wall diameter is 1-5 mm, or 2-3 mm or about 2.7 mm, or lower or higher or intermediate ranges or diameters.

In some embodiments, support structure 712 is shaped to contact the inner wall of tubular structure 714 at one or more discrete portions of the inner wall cross section, for example 1-10, or 2-5, or 4 or lower or higher or intermediate numbers or ranges of portions. In an exemplary embodiment, a cross sectional length of the portion of support structure 712 in contact is 0.01-1 mm, or 0.1-0.5 mm, or 0.2-0.4 mm, or about 0.3 mm or lower or higher or intermediate ranges or lengths.

In some embodiments, support structure 712 is configured to be flexible enough to bend (e.g. repetitively) with bending of the articulated arm e.g. without losing mechanical integrity.

In some embodiments, support structure 712 is shaped to include a trench sized and/or shaped to receive cable 780. In some embodiments, the trench is disposed on an outer surface of the support element. In some embodiments, the support structure trench is configured to hold cable 780 such that, during bending of the support structure at arm articulations, cable 780 remains within the trench.

In some embodiments, the trench holding cable 780 is configured so that a path cable 780 follows along support structure 712 distributes the cable circumferentially around the support structure. For example, in some embodiments, a trench configured to hold cable 780 has a helical shape. In some embodiments, cable 780 follows a single revolution around the support structure in a length which is about 5-30 times, or 10-25 times, or 15-20 times, or lower or higher or intermediate ranges or multiples of a diameter of the support structure.

A potential benefit of the cable being circumferentially distributed around the support structure is reduced total strain on the cable during bending of the support structure. For example, the circumferential distribution meaning, in some embodiments, that when the support structure is bent (e.g. by a surrounding tubular structure) a portion of the cable is compressed and a portion tensioned. In some embodiments, the compression and tension reduce overall and/or average tension on the cable (e.g. by sliding of the cable within) where bending, for example, is by bending of a flexible portion within which the support structure is disposed.

In some embodiments, for a single bendable portion, the cable is distributed circumferentially such that there is a 0.5-5 mm, or 1-3 mm, or about 2 mm length difference between a support structure length and the length of the cable. In some embodiments, the bendable portion is 2-20 cm, or 5-15 cm or about 10 cm long, or lower or higher or intermediate ranges or lengths. In some embodiments, an increase in cable length compared to a length of a shaped portion of the support structure is 0.5-10%, or 0.5-5%, or 1-5%, or 1-3% or about 2%, or lower or higher or intermediate ranges or percentages.

FIG. 7D is a simplified schematic view of a torque cable element including a torque cable 725 and rigid shaft 778, connected by a connector 722 and support structures 782, 712, according to some embodiments of the invention.

In some embodiments, a diameter of 724 is 1.1-1.3 mm.

In some embodiments, a diameter of torque element (e.g. cable) 725 is 0.1-2 mm, or 0.5-1.5 mm, or 0.9-1.1 mm or about 1 mm or lower or higher or intermediate ranges or diameters.

In some embodiments, a diameter of electrical supply cable 780 is 0.1-1 mm, or 0.4-0.5 mm or about 0.45 mm or lower or higher or intermediate ranges or diameters.

FIG. 8A is a simplified schematic of cross section of a portion of a mechanical arm 802, and a side view of an end effector assembly 810, according to some embodiments of the invention.

FIG. 8B is a simplified schematic side view of an end effector assembly 811, according to some embodiments of the invention.

In some embodiments, (e.g. as described and/or illustrated regarding FIGS. 4A-B), mechanical arm 802 includes a plurality of nested tubular structures 828, 826, 824.

In some embodiments, an end effector assembly 810 is an innermost portion of the mechanical arm which, in some embodiments, is coupled, at a distal end of end effector assembly 810 to an end effector (not illustrated in FIG. 8A).

In some embodiments, end effector assembly 810 is an elongated portion, which, in some embodiments, extends through a hollow passageway 823 within an innermost tubular structure 824. In some embodiments, end effector assembly 810 includes one or more bendable torque transfer portions (e.g. torque cable) coupled to one or more rigid shafts. In some embodiments, portion/s of the end effector assembly axially aligned with flexible portions of the mechanical arm are bendable portion/s capable of axially transferring torque. They are "bendable torque transfer portion/s".

In an exemplary embodiment, end effector assembly 810 includes a central torque transfer portion 861 that transfers torque applied to one end of the portion to another end of the portion. In some embodiments, portion/s of torque cable 861 which are disposed within end effector assembly 810 are illustrated in FIGS. 8A-B by a dashed line. In some embodiments, central torque transfer portion 861 includes one or more bendable portion (where, in some embodiments, bendable portion/s include a torque cable) and, optimally, one or more rigid shaft. In some embodiments, portion 861 is bendable at parts of the portion within hollow passageway 823 which axially align with flexible regions of the nested tubular structures regions. For example, in some embodiments, central torque transfer portion 861 is a torque cable for axial portions 881 and 885. In some embodiments, central torque transfer portion 861 is rigid (e.g. a rigid shaft) for axial portion 887. For example, in some embodiments, central torque transfer portion 861 includes a bendable portion for portions 881, 883 and 885 which is coupled to a rigid portion for portion 887. Alternatively, in some embodiments, a rigid portion (e.g. a rigid shaft) connects the two bendable portions, e.g. central torque transfer portion 861 is rigid at axial portion 883 e.g. portion 861 includes two bendable portions and two rigid portions.

In some embodiments, central torque transfer portion 861 is covered by a protective sheath 812. The sheath, in some embodiments, forms a support structure for one or more cables 880. In some embodiments, sheath 812 has a hollow passageway in which portion 861 is disposed. In some embodiments, the sheath hollow passageway and/or portion 861 are sized and/or shaped so that central torque transfer portion 861 rotates freely within the sheath's hollow passageway.

In some embodiments, cable 880 is an electrical supply cable, which, in some embodiments, delivers electrosurgical power to an end effector. In some embodiments, cable 880 changes circumferential position (e.g. is wrapped around the outside of the sheath, e.g. following a helical path) around sheath 812, for one or more axial portions of the sheath. For example, as illustrated in FIG. 8A, for axial portions 881, 883 and 885, cable 880 is wrapped around sheath 812 (where non-visible portions of cable 880 are indicated by a dotted line). In some embodiments, for a proximal axial portion 887, cable 880 maintains a fixed circumferential position on sheath 812.

FIG. 8B illustrates an alternative embodiment of sheath 812 and cable 880 where a plurality of axial portions (e.g. portions 891 and 895 axially aligned with flexible portions of the mechanical arm) cable 880 changes circumferential position (e.g. is wrapped around the outside of the sheath, e.g. following a helical path) around sheath 812. Where a plurality of axial portions (e.g. portions 893 and 897 axially aligned with rigid portions of the mechanical arm), cable 880 maintains a fixed circumferential position on sheath 812.

Exemplary Electrical Supply Cable Connection

FIGS. 9A-C are simplified views of embodiments of electrical connection 902 of an electrical supply cable 980, according to some embodiments of the invention.

In some embodiments, electrical supply cable 980 transfers electrical power from a connection at a motor unit configured to actuate the mechanical arm to the mechanical arm, e.g. including one or more feature as described and/or illustrated in U.S. patent application Ser. No. 15/501,862 and/or U.S. patent application Ser. No. 15/915,235 which are herein incorporated by reference as if fully set forth herein in their entirety.

In some embodiments, electrical supply cable 980 is connected by connection 902 to a slip ring 904 by crimping a connector connected to a proximal end of cable 980 onto a protrusion on slip ring 904. In some embodiments, slip ring 904 is coupled to one or more brush (not illustrated) delivering electrical power supply to the slip ring 904.

Alternatively or additionally, in some embodiments, electrical supply cable 980 is connected to slip ring 904 by an elastic component. In some embodiments, the slip ring includes a hollow into which a semi-circular spring, electrically connected to cable 980 is inserted. The hollow and the spring are sized and/or shaped such that the spring is elastically compressed within the hollow, the elastic force potentially acting to keep the spring in contact with and/or in position within the slip ring.

In some embodiments, electrical supply cable 980 and/or slip ring 904 are coupled to a tubular structure 914 rotation which rotates an end effector coupled to the tubular structure, for example, including one or more features as described and/or illustrated with regards to tubular structure 714, electrical supply cable 780, and end effector 710, FIG. 7B.

In some embodiments, an actuator coupled to a gear 906 actuates rotation of the gear and element/s coupled to the gear, for example, tubular structure 914, and/or a shaft 908 and/or cable 980 an/or slip ring 904.

In some embodiments, shaft 908 provides a surface which is configured to support portion/s of cable 980. In some embodiments, for example, as illustrated in FIG. 9A, one or more additional length of electrical supply cable 980 is disposed along a portion of a length of tubular structure 914 where, in some embodiments, additional length is a length of cable larger than a length required for cable 980 to transverse a route (e.g. along a support structure/s e.g. 712, 782 FIG. 7D) to electrically connect slip ring 904 and a portion of the arm electrified by the cable. In some embodiments, an additional length of electrical supply cable is disposed between gear 906 and slip ring 904.

In some embodiments, the additional length of cable is wrapped around shaft 908 e.g. as illustrated in FIG. 9A. Additional length/s of cable potentially enable removal of a portion of the cable, e.g. if the portion is damaged and/or replacement and/or of a connection where, for example, in some embodiments, the additional length of cable wrapped around the shaft is unwrapped (e.g. transferring from the state illustrated in FIG. 9A to that illustrated in FIG. 9B), from the shaft for example, enabling shortening of the cable whilst maintaining the electrical connection between slip ring 904 and the arm (e.g. the arm end effector).

For example, in some embodiments, if the electrical connection of cable 980 e.g. at a live portion of the arm (e.g. end effector) is faulty, the cable, in some embodiments, the connection is replaced, e.g. by removing a distal end portion of the cable, additional cable length at the proximal end of the electrical cable (e.g. between gear 906 and slip ring 904) being used.

In some embodiments, a cover 910 protects portion/s of cable 980, portion/s for example, disposed between gear 906 and slip ring 904. A potential benefit of the cover is protection and/or prevention of tangling of cable 980 between gear and slip ring 906.

Exemplary Actuation of Exemplary Control Cables

In some embodiments, flexion of one or more articulation of the mechanical arm is controlled by changing tension on one or more cable coupled to the arm (e.g. as illustrated and/or described in document/s listed in the "related applications' section of this document). In an exemplary embodiment, two cables are coupled to each articulation, where flexion is controlled by releasing tension in one of the cables while increasing tension in the other cable.

In some embodiments, tension in the cables is changed by moving a position of a proximal end of the cables. In some embodiments, each cable is connected to a slider at a motor unit at a proximal end of the mechanical arm, where the slider is moved linearly by actuator/s of the motor unit where the actuation and/or motor unit includes one or more feature as described and/or illustrated in U.S. patent application Ser. No. 15/501,862 which is herein incorporated by reference in its entirety.

FIG. 10A is a simplified schematic view of a surgical mechanical arm actuator 1000, according to some embodiments of the invention.

FIG. 10B is a simplified exploded view of a surgical mechanical arm actuator 1000, according to some embodiments of the invention.

In some embodiments, FIG. 10B is an exploded illustration of the surgical mechanical actuator illustrated in FIG. 10A.

In some embodiments, one or more motor (not illustrated) coupled to a gear 1002 is configured to rotate the gear (e.g. coupled by another gear in contact with gear 1002). In some embodiments, gear 1002 is connected to a shaft 1004 which includes threading 1006 and which is rotated by rotation of the gear. In some embodiments, one or more sliders 1008, 1010 are coupled to the shaft, the slider/s including threading 1012 configured so that rotation of shaft threading 1006 generates linear movement of the slider/s with respect to a long axis of shaft 1004. In some embodiments, one or more control cable (not illustrated) is attached to each slider 1008, 1010 with linear movement changing tension on the cable/s. In some embodiments, one or more cables connected to a slider are connected distally to one or more portion of the surgical mechanical arm; the change in tension actuating flexion of one or more joint the arm. In some embodiments, threading of the sliders and/or shaft is configured, upon rotation of gear 1002, to move a first slider 1008 linearly in an opposite direction to a second slider. In an exemplary embodiment, each slider pair actuates flexion of a single articulated arm flexible portion.

FIG. 10C is a simplified schematic of a cable terminal portion 1014 attached to a gear slider 1008, according to some embodiments of the invention.

In some embodiments, one or more cable is connected to a slider by cable terminal portion 1014 where, in some embodiments, the cable terminal portion is sized and/or shaped to be held in position by an indentation 1022 in the slider. For example, in an exemplary embodiment, the cable terminal portion includes a wider portion 1024 which fits into indentation 1022 and a narrow portion 1016 which is held within a slot in the slider where the slot is narrower than the wider portion 1024 of the cable terminal portion. In some embodiments, a screw (not illustrated) is screwed into a hole 1020 (where hole 1020 is optionally a treaded hole), the head of the screw overlapping cable terminal portion 1014.

In some embodiments, one or more cables, and one in an exemplary embodiment (cable/s not illustrated), are attached to cable terminal portion 1014. For example, by swaging where a proximal portion of the cable/s is placed in a hollow 1018 within cable terminal portion 1014, pressure is applied to the terminal portion to narrow hollow 1018 around the cable.

FIG. 11 is a simplified sectional view of a surgical mechanical arm actuator 1100, according to some embodiments of the invention. In some embodiments, actuator 1100 includes one or more feature as described and/or illustrated regarding actuator 1000 FIGS. 10A-B.

In some embodiments, sliders 1108, 1110 of a surgical mechanical arm actuator have different dimension/s. In an exemplary embodiment, a thickness 1150 of a first slider 1108 is different than a thickness 1152 of a second slider 1110. For example, in some embodiments, the first slider thickness 1150 is smaller than the second slider thickness 1152, for example, by 1-50%, or 1-30%, or 5-30%, or 15-30%, or about 25%, or lower or higher or intermediate ranges or percentages. In some embodiments, a sector angle 1156 of an annulus of first slider 1108 is smaller than a sector angle 1158 of an annulus of second slider 1110, where, in some embodiments, the annuli of the sliders have the same inner and outer radii, for example, where the first slider sector angle 1156 is 50-98%, or 60-95%, or 70-85%, or lower or higher or intermediate ranges or percentages of second slider sector angle 1158.

In some embodiments, sliders move axially with respect to a shaft 1104 and are held in position within a tubular structure 1154 by rails 1126, 1128.

In some embodiments, the position of rails 1126, 1128 is configured for different thickness and/or sector angle of the sliders. Potentially easing accurate manufacture of the actuator as, once the rails are positioned, a hollow for each slider is sized and/or shaped differently for the different sliders.

Exemplary Methods of Manufacture

FIG. 12 is a flow chart of a method of manufacture of a mechanical articulated arm, according to some embodiments of the invention.

In some embodiments, one or more portion of a method of manufacture is automated, for example, at least a portion of manufacture being robotically automated. Alternatively or additionally, in some embodiments, manufacture is manual and/or includes manual portions.

At 1200, in some embodiments, a plurality of tubes are selected. In some embodiments, dimensions of the tube/s are selected, for example, for a specific application. In some embodiments, for example, a maximum cross-sectional dimension for the arm is selected and/or an outermost tubular structure cross-sectional dimension is selected, and inner tube dimensions are determined by the selected dimensions and optionally control cable number and/or cross-sectional dimension.

In some embodiments, a size and/or wall thickness of one or more tubes is selected to provide the tubular structure with sufficient strength (e.g. for an application). In some embodiments, a size and/or wall thickness of one or more tube is selected to provide the tubular structure with sufficient strength based on a given size (e.g. cross-sectional dimension) of one or more control cable for control of a portion of the surgical mechanical arm. In some embodiments, control cable/s are selected based on required strength and/or size.

For example, in some embodiments, one or more tube has a constant inner and/or outer diameter. In some embodiments, one or more tube has dimension/s which vary along the length of the tube, for example, tapering.

At 1202, in some embodiments, one or more tubular structures are prepared, for example, by cutting and/or welding e.g. of one or more tubes.

In some embodiments, preparation of a tubular structure includes cutting one or more trenches within the tube, where, in some embodiments, the trench is formed by partially cutting through a wall of the tube.

In some embodiments the trench is milled from the tube, which is, for example, in some embodiments, a tube with uniform wall thickness over the length of the tube and/or over the tube cross section.

In an exemplary embodiment, two trenches are cut in a tube (e.g. for the outermost and intermediate tubes, in an embodiment which includes three tubes), opposite each other. In some embodiments, the two trenches are cut such that the circumference of a tube cross section between the two trenches in both clockwise directions is equal. In some embodiments, trenches are located diametrically opposing each other, such that the lengths of the arcs (along the circumference of the tube) are equal. In some embodiments, trench dimensions for one or more trench (e.g. for both of two trenches, where the tube has two trenches) are about the same e.g. the same length and/or width and/or depth and/or cross-sectional area.

In an exemplary embodiment, more than one trench (e.g. all trenches) of a tubular structure are milled at the same time, for example, where the same axial portion of more than one trench is milled concurrently.

In some embodiments, preparation of a tubular structure includes attaching a cover to a trench e.g. a cover to each trench. In some embodiments, the cover is welded into position over the trench. In some embodiments, the cover is positioned such that the cover does not protrude from a surface of the tube. For example, in some embodiments, the cover is attached within the trench where, e.g. edges of the cover are attached to walls of the trench.

In some embodiments, preparation of a tubular structure includes laser cutting portion/s of a tube which, in some embodiments, follows cutting and/or covering of tubular structure trenches where, in some embodiments, each tubular structure is cut to provide at least one bendable torque transfer portion and, optionally, a flexible section which is e.g. bendable in a single plane.

In some embodiments, preparation of a tubular structure includes inserting one or more control cable into trench/s. In some embodiments, a control cable is inserted into each trench. In some embodiments, a cable is sufficiently stiff to be pushed through at least a portion of the trench, for example, from an opening in the trench at an end of the tubular structure. In some embodiments, a jig is used for cable insertion, the jig, for example, includes one or more of a support (e.g. mechanical, structural support) to hold tubular structure/s and/or cable/s.

In an exemplary embodiment, three tubular structures are prepared. In some embodiments, the three tubular structures include one or more features as illustrated and/or described regarding tubular structures 428, 426, 424, FIGS. 4A-B and/or 828, 826, 824, FIG. 8A.

In some embodiments, an end effector is attached to a tubular structure. In an exemplary embodiment, the end effector is attached to the smallest diameter (innermost) tubular structure. In some embodiments, an end effector structure including an end effector, cable for actuation of the end effector and, optionally, an electrical supply cable are coupled to the innermost tubular structure.

At 1204, in some embodiments, the tubular structures are nested one inside each other, e.g. the structure including one or more feature as described and/or illustrated tubular structures 424, 426, 428 FIGS. 4A-B and/or 828, 826, 824, FIG. 8A.

In some embodiments, more than two tubular structures e.g. 3-10 are nested. In an exemplary embodiment, 3 tubular structures are nested, a first tubular structure positioned within a second tubular structure, where the second tubular structure is positioned within a third tubular structure. Optionally, in some embodiments, the tubular structures are coupled to each other by one or more component and/or connector. In some embodiments, one or more coupling prevents movement of the tubular structures with respect to each other, for example, in an axial direction and/or in a radial direction. In some embodiments, the mechanical arm includes one or more bearing where a bearing, in some embodiments, prevents axial movement between two tubular structures while, in some embodiments, allowing one or more of the tubular structures to rotate about a tubular structure long axis independently.

In some embodiments, the tubular structures are coupled by connection of proximal ends of the structures. For example, in some embodiments, the surgical mechanical arm includes a handle assembly which, in some embodiments, holds a proximal portion of each tubular structure. In some embodiments, the handle assembly prevents axial movement of the tubular structures with respect to each other.

At 1206, in some embodiments, the mechanical arm is connected to one or more actuator.

At 1208, in some embodiments, at least a portion of the mechanical arm is covered. For example, by one or more electrically insulating and/or water impermeable cover. In some embodiments, the surgical mechanical arm is sterilized.

At 1210, in some embodiments, the mechanical arm is calibrated. For example, by coupling the mechanical arm to a motor unit where movement of the arm is controlled by a controller, calibration involving, for example, commanding movement of the arm using the controller, measuring the movement of the arm, and aligning commanded movement with actual movement. In some embodiments, a dedicated jig including a motor unit to which a controller is coupled, is used to calibrate the mechanical arm.

FIG. 13 is a flow chart of a detailed method of manufacture of an articulated surgical arm, according to some embodiments of the invention.

In some embodiments, rectangular elements of FIG. 13 indicate components and elongated hexagon elements indicate steps of the flow chart.

In some embodiments, tubular structures of the articulated arm are prepared, for example, where the preparation includes one or more features as described regarding step 1202, FIG. 12.

Exemplary Shoulder and Elbow Assembly Construction

At 1300, in some embodiments, a shoulder tube (also herein termed "outermost tube") is provided.

At 1302, in some embodiments, trench/es are milled in the shoulder tube.

At 1304, in some embodiments, cover/s are welded (e.g. laser welded) to cover trench/es (where the cover is a thin ribbon of material, for example, a shims ribbon 1306).

At 1308, in some embodiments, the shoulder tubular structure (also herein termed "outermost tubular structure") is laser marked.

At 1310, in some embodiments, bendable and/or flexible portion/s are laser cut in the shoulder tubular structure, where, in some embodiments, cutting is using the laser markings. In an exemplary embodiment, cutting of the shoulder tubular structure includes cutting a single flexible portion.

At 1312, in some embodiments, a shoulder proximal connector 1314 is connected (e.g. by welding) to a proximal portion (e.g. proximal end) of the shoulder tube, where the shoulder proximal connector, in some embodiments, is configured to fit within a handle assembly.

In some embodiments, one or more of laser marking, laser cutting and welding are performed using the same laser and/or same type of laser.

At 1316, in some embodiments, one or more actuation cable is positioned, where, in some embodiments, an actuation cable is inserted into each trench of the shoulder tubular structure. In some embodiments, actuation cable/s 1318 are swaged onto terminal/s 1320 e.g. each actuation cable is swaged to a terminal at a proximal and/or at a distal end of the cable. Where swaging involves, in some embodiments, inserting a portion of the cable (e.g. an end of the cable) into an inlet in the terminal and then compressing the terminal to attach the parts.

At 1322, in some embodiments, actuation cable terminals are attached (e.g. by welding into position). In some embodiments, each actuation cable is welded into position at a distal end to a portion of the mechanical arm and/or at a proximal end of the cable to an actuator slider (e.g. the slider and/or terminal including one or more feature as described and/or illustrated regarding FIGS. 10A-C and/or FIG. 11).

At 1324, in some embodiments, an elbow tube (also herein termed "intermediate tube") is provided.

At 1326, in some embodiments, trench/es are milled in the elbow tube.

At 1328, in some embodiments, cover/s 1330 are welded (e.g. laser welded) to cover trench/es (where the cover/s include, for example, one or more thin ribbon of material with ends which are wider than a body of the material, herein termed "dog bone shims ribbon").

At 1332, in some embodiments, the elbow tubular structure (also herein termed "intermediate tubular structure") is laser marked.

At 1334, in some embodiments, bendable and/or flexible portion/s are laser cut in the elbow tubular structure. In an exemplary embodiment, a flexible portion and a bendable torque transfer portion are cut, where, in some embodiments, a rigid (e.g. un-cut portion) is disposed between the flexible and bendable portions in the elbow tubular structure.

At 1336, in some embodiments, a shoulder bearing terminal is welded to the elbow tubular structure. Where, in some embodiments, the shoulder bearing terminal is a protrusion on the elbow tubular structure which fits an indentation in a shoulder bearing e.g. including one or more features as illustrated and/or described regarding FIG. 14D.

At 1338, in some embodiments, actuation cable/s are positioned, where, in some embodiments, an actuation cable is inserted into each trench of the elbow tubular structure. In some embodiments, actuation cable/s 1318 and actuation cables are swaged to terminals 1320 e.g. using one or more features as described regarding step 1316.

At 1340, in some embodiments, actuation cable/s are connected In some embodiments, each actuation cable is welded into position at a distal end to a portion of the mechanical arm and/or at a proximal end of the cable to an actuator slider (e.g. the slider and/or terminal including one or more features as described and/or illustrated regarding FIGS. 10A-C and/or FIG. 11).

At 1344, in some embodiments, the elbow tubular structure is inserted into the shoulder tubular structure (nested within) and a bearing 1342 is used to couple the tubular structures where, in some embodiments, bearing 1342 prevents axial movement of the tubular structures with respect to each other and/or allows rotation of one or both of the tubular structures with respect to the other tubular structure. The coupled tubular structure herein being termed a "shoulder-elbow assembly".

At 1303, in some embodiments, a passivation procedure is performed on the shoulder-elbow assembly, for example, citric passivation (e.g. citric passivation ASTM-A-967).

At 1305, in some embodiments, portion/s of the shoulder-elbow assembly are cleaned and/or degreased.

Exemplary Wrist Gripper Assembly

In some embodiments, a wrist gripper assembly includes an end effector (which, in some embodiments, is a gripper), a wrist tubular structure (also herein termed "innermost tubular structure") coupled to the end effector, and an innermost torque transfer assembly. Where, in some embodiments, the innermost torque transfer assembly transfers torque to the end effector to actuate the end effector (e.g. to open and/or close the gripper). In some embodiments, rotation of the wrist tube about a wrist tube long axis rotates the end effector. In some embodiments, the innermost torque transfer assembly includes one or more electrical supply cables and/or one or more protective sleeves.

At 1366, in some embodiments, a wrist tube is provided (also herein termed "innermost tube").

At 1368, in some embodiments, the wrist tube is laser marked.

At 1370, in some embodiments, one or more portions of the wrist tube is laser cut to form joints, to construct a wrist tubular structure (also herein termed "innermost tubular structure"). In an exemplary embodiment, a first and a second bendable torque transfer portion are cut in the wrist tube with, in some embodiments, a rigid (e.g. uncut) portion therebetween.

At 1372, in some embodiments, a passivation procedure is performed on the wrist tubular structure assembly, for example, citric passivation (e.g. citric passivation ASTM-A-967).

At 1374, in some embodiments, the wrist tubular structure is cleaned and/or degreased. At 1346, in some embodiments, torque coupler/s and/or a gripper screw bearing are provided.

At 1348, in some embodiments, a torque cable and/or a torque cable protective sleeve are provided.

At 1350, in some embodiments, a torque shaft and/or a torque shaft protective sleeve are provided.

In some embodiments, a torque shaft is inserted into a torque shaft protective sleeve (also herein termed "support structure").

In some embodiments, a torque cable is inserted into a torque cable protective sleeve (also herein termed "support structure").

At 1354, in some embodiments, a gripper actuation screw is provided.

At 1356, in some embodiments, the gripper actuation screw is treated, for example heat treated (e.g. 17-4 PH H900 heat treatment).

At 1352, in some embodiments, the torque shaft is coupled to the torque cable (e.g. by swaging, optionally using a terminal). In some embodiments, the gripper actuation screw is coupled to the torque cable by a gripper screw bearing, for example, by swaging.

At 1358, in some embodiments, one or more of the connected parts (torque shaft, torque cable, gripper actuation screw, protective sleeves) are cleaned and/or degreased.

At, 1360, in some embodiments, one or more of a gripper pressure-contact plate, a bipolar insulation plate, a portion including gripper teeth (herein termed "a biter") and a 1.3 mm pin are provided.

At 1362, in some embodiments, an O-ring and a power supply cable are provided.

At 1364, in some embodiments, one or more of the parts provided in steps 1360 and/or 1362 are cleaned and/or degreased.

At 1376, in some embodiments, a fixed jaw portion and a monopolar tip are provided. At 1378, in some embodiments, the monopolar tip is welded to the fixed jaw portion. At 1380, in some embodiments, a passivation procedure is performed on the fixed jaw portion excluding the monopolar tip, for example, citric passivation (e.g. citric passivation ASTM-A-967).

At 1382, the fixed jaw portion is partially coated with an insulator, for example, coated with parylene. In some embodiments, coating is applied using vapor disposition. In some embodiments, portions that are not to be coated are protected with a buffer which is then removed after the coating procedure.

At 1384, in some embodiments, the fixed jaw portion and/or monopolar tip are cleaned and/or degreased.

At 1386, in some embodiments, a dynamic jaw portion is provided.

At 1388, in some embodiments, the dynamic jaw portion is laser marked.

At 1390, in some embodiments, a passivation procedure is performed on the dynamic jaw portion for example, citric passivation (e.g. citric passivation ASTM-A-967).

At 1392, the dynamic jaw portion is partially coated with an insulator, for example, coated with parylene. In some embodiments, coating is applied using vapor disposition. In some embodiments, portions that are not to be coated are protected with a buffer which is then removed after the coating procedure.

At 1394, in some embodiments, the dynamic and fixed jaw portions are coupled by one or more pin 1396. In some embodiments, a slider coupled to the torque screw actuates opening and/or closing of the tool jaws, for example, by effecting rotation of the dynamic jaw portion about the pin/s. Actuation, for example, includes one or more feature as described and/or illustrated in U.S. patent application Ser. No. 15/915,237 which is herein incorporated by reference it its entirety.

At 1398, in some embodiments, dynamic jaw portion part/s are cleaned and/or degreased.

At 1301, in some embodiments, a wrist gripper assembly is constructed by one or more of:

Coupling the power supply cable (provided in step 1362) to the torque shaft support structure and the torque cable support structure.

Electrically connecting the power supply cable to one of the jaw portions e.g. to the monopolar electrosurgical tip;

Inserting connected parts (e.g. one or more of; torque shaft, torque cable, gripper actuation screw, support structure) into the wrist tubular structure; and Fitting an O-ring at a distal end of the wrist gripper assembly, the O-ring potentially sealing the arm (e.g. hollow portions of the arm) from fluids and/or other debris (e.g. surgical debris) at the tool.

In some embodiments, at 1307, the gripper assembly is inserted into (e.g. nested within) the shoulder-elbow assembly. In some embodiments, bendable portions of the gripper assembly are aligned with flexible portions of the shoulder-elbow assembly. In some embodiments, the gripper assembly and the shoulder assembly are coupled by a wrist bearing.

At 1309, in some embodiments, shoulder actuator assembly part/s are provided, for example, including one or more of a shoulder actuator screw, a shoulder bending nut, a shoulder straightening nut, nut fastening screw/s, shoulder actuator housing part/s, a shoulder actuator spring, and a washer for the shoulder spring.

At 1311, in some embodiments, one or more parts provided in step 1309 are cleaned and/or degreased.

At 1313, in some embodiments, a shoulder actuator assembly is assembled, e.g. using parts provided in step 1311. In some embodiments, the shoulder actuator assembly is coupled to the shoulder tubular structure, the coupling configuring the shoulder actuator assembly to actuate rotation of the shoulder tube and/or flexion of the shoulder joint.

At 1315, in some embodiments, elbow actuator assembly part/s are provided, for example, including one or more of an elbow actuator screw, an elbow bending nut, an elbow straightening nut, nut fastening screw/s, elbow actuator housing part/s, an elbow actuator spring.

At 1317, in some embodiments, one or more parts provided in step 1315 are cleaned and/or degreased.

At 1319, in some embodiments, an elbow actuator assembly is assembled, e.g. using parts provided in step 1315. In some embodiments, the elbow actuator assembly is coupled to the elbow tubular structure, the coupling configuring the elbow actuator assembly to actuate rotation of the elbow tube and/or flexion of the elbow joint.

At 1321, in some embodiments, slip ring assembly part/s are provided, for example, including one or more of a wrist gear, a monopolar slip ring, a bipolar slip ring, and a collet.

At 1323, in some embodiments, one or more parts provided in step 1321 are cleaned and/or decreased.

At 1325, in some embodiments, a slip ring assembly is assembled, e.g. using parts provided in step 1321. In some embodiments, the slip ring assembly is coupled to the inner tubular structure and the electrical supply cable is electrically connected to one of the slip rings.

At 1327, in some embodiments, parts are provided for an arm protection assembly, parts including for example, one or more sleeve and/or shrink wrap 1329 (e.g. electrically insulating shrink wrap, e.g. polyester shrink wrap).

At 1331, in some embodiments, one or more of the parts provided in step 1327 are cleaned and/or degreased.

At 1333, in some embodiments, an arm protection assembly is assembled, e.g. using parts provided in step 1327. In some embodiments, part/s provided in step 1327 are connected to the articulated arm e.g. by placing portion/s of the arm into the sleeve/s and/or shrink wrap.

In some embodiments, a proximal portion of the arm which, in some embodiments, includes only rigid portions, is covered by a shrink wrap sleeve which is then fitted to the arm (e.g. by heat treatment). In some embodiments, a distal portion of the arm which, in some embodiments, includes flexible portions, is placed within an elastic silicone rubber sleeve which is sized and/or shaped to fit the arm portion on which it is disposed. In some embodiments, one or more bearing allows rotation of one or more portion of the arm with respect to a sleeve. For example, in an exemplary embodiment, a bearing at a distal end of the arm separates between the silicone rubber sleeve and the tool, for example, enabling rotation of the tool within the sleeve. In some embodiments, the silicone rubber sleeve is covered by an additional sleeve, which, in some embodiments, is shrink wrap which is treated to fit the shrink wrap to underlying arm and/or silicone sleeve structure.

At 1335, in some embodiments, parts are provided for an arm handle assembly, for example, including one or more of handle part. Where, in some embodiments, handle part/s include one or more of; portion/s which hold the arm and/or separate portion/s of the arm; protrusion/s sized and/or shaped to provide handles for a user to manipulate the arm with.

At 1337, in some embodiments, one or more of the parts provided in step 1335 are cleaned and/or degreased.

At 1339, in some embodiment, an arm handle assembly is assembled, e.g. using parts provided in step 1335 where, in some embodiments, assembling the handle assembly couples the handle assembly to a proximal portion of the arm. In some embodiments, the handle assembly is coupled to a portion of the arm including arm actuators. In some embodiments, the arm handle assembly is then coupled to a proximal portion of the articulated arm. In some embodiments, one or more portion of the handle assembly (e.g. the handles and/or other portion/s) are constructed from plastic and/or electrically insulating material.

At 1351, in some embodiments, parts are provided for arm packaging, for example, including one or more of die cut cards and sterile pouch/es. In some embodiments, portion/s of the die cut cards are folded to create arm holders, the arm is positioned on one or more cut card (e.g. die cut card/s) and portion/s of the die cut card/s are folded and/or connected to hold the arm in position on the card/s.

At 1341, the arm (e.g. attached to the die cut card/s) is inserted into a sterile pouch.

At 1343, in some embodiments, the packaged arm (e.g. within the sterile pouch) is sterilized.

At 1347, in some embodiments, arm unit box packaging part/s are provided e.g. one or more of a cardboard box, protective foam/s, device label/s.

At 1345, in some embodiments an arm unit box packaging is constructed, for example, using parts provided in step 1347.

At 1349, in some embodiments, the packaged sterilized arm is placed into the arm unit box packaging.

Exemplary Bearings

FIG. 14A is a simplified schematic of a portion of a surgical mechanical arm, according to some embodiments of the invention.

In some embodiments, a surgical mechanical arm includes a wrist bearing 1402, also herein termed an inner-intermediate tubular structure bearing. In some embodiments, bearing 1402 enables independent rotation of one or both of an inner tubular structure (which is, in some embodiments, coupled to a tool) and an intermediate tubular structure. In some embodiments, bearing 1402 prevents axial movement of the tubular structures with respect to each other.

In some embodiments, the surgical mechanical arm includes a shoulder bearing 1406, also herein termed an intermediate-outer tubular structure bearing. In some embodiments, a first flexible portion 1402 connects bearings 1402, 1406. In some embodiments, bearing 1406 enables independent rotation of one or both of an outer tubular structure and an intermediate tubular structure. In some embodiments, bearing 1406 prevents axial movement of the tubular structures with respect to each other.

In some embodiments, one or both of bearings 1402, 1406 are sealed e.g. with grease (e.g. biocompatible grease) where grease and/or close fitting between parts seals the bearing and/or arm (e.g. hollow portion/s of the arm).

FIG. 14B is a simplified schematic of a distal portion of a surgical mechanical arm including a tool 1410 and a wrist bearing 1402, according to some embodiments of the invention.

FIG. 14C is a simplified schematic of a wrist bearing 1402, according to some embodiments of the invention. In some embodiments, the wrist bearing of FIG. 14C is an enlarged wire-frame view of the wrist bearing of FIG. 14B and/or FIG. 14A.

In some embodiments, bearing 1402 includes a connector which connects the inner and intermediate tubular structures. For example, in some embodiments, bearing includes a pin 1412 which is placed into a hollow passageway 1408 in a bearing housing. In some embodiments, pin 1412 and/or hollow passageway 1408 are sized and/or shaped for the pin to closely fit within the hollow passageway, e.g. potentially holding the pin within the passageway.

FIG. 14D is a simplified schematic cross section of a shoulder bearing 1406, according to some embodiments of the invention.

In some embodiments, bearing 1406 includes a protrusion 1418 (also termed, within this document "bearing terminal") mounted on an intermediate tubular structure 1414. In some embodiments, the protrusion is attached to intermediate tubular structure 1414 e.g. by welding.

In some embodiments, bearing 1406 includes a connector 1420 which is in some embodiments, attached to an outer tubular structure 1415 e.g. by welding. In some embodiments, connector 1420 includes a recess sized and/or shaped to receive protrusion 1418.

Exemplary Dimensions

In some embodiments, an outer diameter of an outer tubular structure (e.g. 428 FIGS. 4A-B, 528 FIG. 5A) is 1-20 mm, or 5-10 mm, or about 8 mm, or lower or higher or intermediate ranges or diameters. In some embodiments, an inner diameter of the outer tubular structure is 1-15 mm, or 2-10 mm, or 5-7 mm, or about 6 mm, or lower or higher or intermediate ranges or diameters. In some embodiments, a thickness of a wall of the outer tubular structure is 0.1-2 mm, or 0.5-1.5 mm, or about 0.9 mm or lower or higher or intermediate ranges or thicknesses.

In some embodiments, an outer diameter of an intermediate tubular structure (e.g. 426 FIGS. 4A-B. 526 FIG. 5A) is 1-10 mm, or 3-7 mm, or about 5.5 mm, or lower or higher or intermediate ranges or diameters. In some embodiments, an inner diameter of the intermediate tubular structure is or about 1-10 mm, or 2-6 mm, or about 4 mm, or lower or higher or intermediate ranges or diameters. In some embodiments, the thickness of the wall of the intermediate tubular structure is 0.1-2 mm, or 0.5-1.5 mm, or about 0.89 mm or lower or higher or intermediate ranges or thicknesses.

In some embodiments, the outer diameter of an inner tubular structure (e.g. 424 FIGS. 4A-B. 524 FIG. 5A) is 1-7 mm, or 2-5 mm, or about 3.5 mm, or lower or higher or inner ranges or diameters. In some embodiments, the inner diameter of the inner tubular structure is 1-5 mm, or 2-3 mm, or about 2.7 mm, or lower or higher or intermediate ranges or diameters. In some embodiments, a thickness of a wall of the inner tubular structure is 0.1-1 mm, or 0.2-0.6 mm, or about 0.4 mm or lower or higher or intermediate ranges or thicknesses.

In some embodiments, a total length of an articulated arm is 50-200 cm, or 100-200 m, or 100-150 cm, or about 130 cm, or lower or higher or intermediate ranges or lengths. In some embodiments, a total length of flexible portions of the arm is 5-30 cm, or 10-30 cm, or about 20 cm long or lower or higher or intermediate ranges or lengths. In some embodiments, a percentage of a length of an articulated arm which is flexible is 1-30%, or 5-20% or about 15% or lower or higher or intermediate ranges or percentages.

General

It is expected that during the life of a patent maturing from this application many relevant surgical mechanical tools will be developed and the scope of the term surgical mechanical tool is intended to include all such new technologies a priori.

As used herein the term "about" refers to +20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. An articulated arm comprising:
    a tubular structure comprising a plurality of coupled longitudinal sections comprising:
        one or more rigid portions; and
        at least one flexible portion comprising a plurality of connected annular portions;
    wherein said tubular structure comprises:
        a trench formed along a longitudinal axis of said tubular structure and extending along said plurality of coupled longitudinal sections; and
        a cover attached to said tubular structure and covering at least a portion of said trench, the cover being at least partly recessed within said trench.

2. The articulated arm according to claim 1, wherein said cover completes said tubular structure to a tubular shape.

3. The articulated arm according to claim 1, wherein said trench and said cover are sized and shaped such that an outer contour of said cover is contained by an outer contour of said tubular structure.

4. The articulated arm according to claim 1, comprising at least one flange disposed along at least a portion of at least one edge of said trench, where said cover is attached to said at least one flange.

5. The articulated arm according to claim 1, wherein said trench is defined by walls, and said cover is attached to the walls of said trench.

6. The articulated arm according to claim 1, comprising an elongated element for control of said articulated arm, where said elongated element is:
    disposed within said trench;
    at least partially enclosed within said trench by said cover; and
    coupled to a portion of said tubular structure distal of said at least one flexible portion.

7. The articulated arm according to claim 6, wherein flexion of said at least one flexible portion is controlled by changing tension on said elongated element.

8. The articulated arm according to claim 1, wherein said cover includes at least one wide portion having a larger width than an average width of the cover, said wide portion being axially aligned with said one or more rigid portions.

9. The articulated arm according to claim 1, wherein said cover includes a first and a second wide portion, each having a larger width than an average width of the cover and disposed at a proximal and a distal end of said cover respectively, wherein said first and said second wide portion are each axially disposed at said one or more rigid portions of said tubular structure.

10. The articulated arm according to claim 1, comprising a second tubular structure disposed within a central hollow passageway of said tubular structure.

* * * * *